(12) United States Patent
Kurihara et al.

(10) Patent No.: US 10,463,725 B2
(45) Date of Patent: Nov. 5, 2019

(54) IMMUNITY INDUCING AGENT

(71) Applicant: TORAY INDUSTRIES, INC., Tokyo (JP)

(72) Inventors: Akira Kurihara, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/882,307

(22) Filed: Oct. 13, 2015

(65) Prior Publication Data
US 2016/0030540 A1   Feb. 4, 2016

Related U.S. Application Data

(62) Division of application No. 14/118,271, filed as application No. PCT/JP2012/062750 on May 18, 2012, now abandoned.

(30) Foreign Application Priority Data

May 19, 2011 (JP) ................................. 2011-112181

(51) Int. Cl.

| A61K 39/00 | (2006.01) |
| A61K 14/47 | (2006.01) |
| A61K 45/06 | (2006.01) |
| A61K 31/7088 | (2006.01) |
| A61K 38/00 | (2006.01) |
| A61K 38/20 | (2006.01) |
| A61K 38/21 | (2006.01) |
| A61K 38/17 | (2006.01) |

(52) U.S. Cl.
CPC ...... *A61K 39/0011* (2013.01); *A61K 31/7088* (2013.01); *A61K 38/1709* (2013.01); *A61K 38/20* (2013.01); *A61K 38/208* (2013.01); *A61K 38/21* (2013.01); *A61K 38/212* (2013.01); *A61K 38/215* (2013.01); *A61K 38/217* (2013.01); *A61K 45/06* (2013.01); *C07K 14/47* (2013.01); *A61K 38/00* (2013.01); *A61K 39/00* (2013.01); *A61K 2039/53* (2013.01)

(58) Field of Classification Search
None
See application file for complete search history.

(56) References Cited

U.S. PATENT DOCUMENTS

| 5,595,756 A * | 1/1997 | Bally .................. A61K 9/1272 264/4.1 |
| 5,698,396 A | 12/1997 | Pfreundschuh |
| 6,429,304 B1 | 8/2002 | Vale et al. |
| 2004/0005560 A1 | 1/2004 | Isogai et al. |

2004/0078804 A1   4/2004   Yue et al.

FOREIGN PATENT DOCUMENTS

| WO | WO-0153312 A1 * | 7/2001 | ............. C07K 14/47 |
| WO | WO2001053312 A1 * | 7/2001 | |
| WO | WO 2001053312 A1 | 7/2001 | |
| WO | WO 01/85942 A2 | 11/2001 | |

OTHER PUBLICATIONS

Bowie et al. Deciphering the message in protein sequences: tolerance to amin oacid substitutions.Science, 247:1306-1310, 1990.*
Whisstock et al. Prediction of protein function from protein sequence and structure. Quarterly Reviews in Biophysics. 36(3):307-340, 2007.*
Lazar et al. Transforming Growth Factor alpha: Mutation of Aspartic Acid 47 and Leucine 48 Results in Different Biological Activities. Molecular Cellular Biology. 1988; 8(3):1247-1252.*
Erickson et al. Searching for 13q key players in esophogeal squamous cell carcinogensis by qRT_PCR of microdissected tissues. Cancer Biomarkers. 4(3): 139-140.*
Ye et al. Aberrant expression of katanin p60 in prostate cancer bone metastasis. Prostate, 2012; 72(3):291-300.*
Heppner et al. Tumor heterogeneity: biological implications and therapeutic consequences. Cancer Metastasis Review 2:5-23; 1983.*
Jain RK. Barriers to drug delivery in solid tumors. Scientific American, Jul. 1994, 58-65.*
Erickson et al. Searching for 13q key players in esophogeal squamous-cell carcinogenesis by qRT-PCR of microdissected tissues. Cancer Biomarkers, 2008; 4(3): 139-140 (Year: 2008).*
Ye et al. Aberrant expression of katanin p60 in prostate cancer bone metastasis. Prostate, 2012; 72(3):291-300 (Year: 2012).*
Buonaguro et al. Translating tumor antigens into cancer vaccines. Clinical and Vaccine Immunology, 2011; 18(1):23-34 (Year: 2011).*
Heppner et al. Cancer Metastasis Review 2:5-23; 1983 (Year: 1983).*
Jain RK. Scientific American, Jul. 1994, 58-65 (Year: 1994).*
Bowie et al., Deciphering the Message in Protein Sequences: Tolerance to Amino Acid Substitutions, Science, vol. 247, pp. 1306-1310, 1990.
Erickson et al., "Searching for 13q key players in esophogeal squamous-cell carcinogenesis by qRT-PCR of microdissected tissues", Cancer Biomarkers. vol. 4, No. 3, pp. 139-140.
Extended European Search Report for European Application No. 12784927.1, dated Oct. 6, 2014.
Heppner et al., "Tumor heterogeneity: biological implications and therapeutic consequences", Cancer Metastasis Review, vol. 2, pp. 5-23, 1983.
International Search Report for International Application No. PCT/JP2012/062750 dated Jun. 26, 2012.

(Continued)

*Primary Examiner* — Vanessa L. Ford
*Assistant Examiner* — Sandra E Dillahunt
(74) *Attorney, Agent, or Firm* — Birch, Stewart, Kolasch & Birch, LLP

(57) ABSTRACT

Provided is a method for inducing immunity for therapy of a cancer(s). The method includes the step of administering to an individual with cancer at least one polypeptide selected from the polypeptides (a) or (b) below, and/or a recombinant vector(s) that comprise(s) a polynucleotide(s) encoding the at least one polypeptide, the recombinant vector(s) being capable of expressing the polypeptide(s) in vivo: (a) a polypeptide in any one of the amino acid sequences of SEQ ID NOs: 2, 4, 8, 10 and 12; and (b) a polypeptide having a sequence identity of not less than 95% to the polypeptide (a).

6 Claims, 3 Drawing Sheets

Specification includes a Sequence Listing.

(56) References Cited

OTHER PUBLICATIONS

Lazar et al., "Transforming Growth Factor ox: Mutation of Aspartic Acid 47 and Leucine 48 Results in Different Biological Activities", Molecular Cellular Biology, vol. 8, No. 3, pp. 1247-1252, 1988.
Rigden et al., "Ab initio protein modelling reveals novel human MIT domains," FEBS Letters, vol. 583, 2009 (available online Feb. 12, 2009), pp. 872-878.
Sahin et al., "Human neoplasms elicit multiple specific immune responses in the autologous host," Immunology, Proc. Natl. Acad. Sci., vol. 92, Dec. 1995, pp. 11810-11813.
Van Der Bruggen et al., "A Gene Encoding an Antigen Recognized by Cytolytic T Lymphocytes on a Human Melanoma," Science, vol. 254, Dec. 13, 1991, pp. 1643-1647.
Whisstock et al., "Prediction of protein function from protein sequence and structure", Quarterly Reviews in Biophysics, vol. 36, No. 3, pp. 307-340, 2007.

* cited by examiner

SEQUENCE LISTING

<160> NUMBER OF SEQ ID NOS: 29

<210> SEQ ID NO 1
<211> LENGTH: 1760
<212> TYPE: DNA
<213> ORGANISM: Canis familiaris
<220> FEATURE:
<221> NAME/KEY: CDS
<222> LOCATION: (97)..(1569)
<223> OTHER INFORMATION:

<400> SEQUENCE: 1

```
gccgcccag  ctgcagggcc  tcgggcctgc  ggcgcctctg  accctcccag  gttgctgctg          60
ccgctcggtg  ccgaacctgt  aggtctctgc  aagaag atg aat ttg gct gag att         114
                                          Met Asn Leu Ala Glu Ile
                                           1               5 tgt gac aat gca aag aaa gga aga gaa tat gca ctt ctt ggg aac tat         162
Cys Asp Asn Ala Lys Lys Gly Arg Glu Tyr Ala Leu Leu Gly Asn Tyr
             10                  15                  20 gac tca tca atg gta tat tac cag ggg gtg ata cag cag att cag aga         210
Asp Ser Ser Met Val Tyr Tyr Gln Gly Val Ile Gln Gln Ile Gln Arg
         25                  30                  35 cat tgc cag tca gtc aga gac cca gct gtc aaa ggc aaa tgg caa cag         258
His Cys Gln Ser Val Arg Asp Pro Ala Val Lys Gly Lys Trp Gln Gln
     40                  45                  50 gtt cgg cag gaa tta ttg gaa gaa tat gaa caa gtt aaa aac att gtc         306
Val Arg Gln Glu Leu Leu Glu Glu Tyr Glu Gln Val Lys Asn Ile Val
 55                  60                  65                  70 agc act ttg gag agt ttt aaa atg gac aag ccc cca gat ttc cct gtg         354
Ser Thr Leu Glu Ser Phe Lys Met Asp Lys Pro Pro Asp Phe Pro Val
                 75                  80                  85 tcc tgt caa gat gaa cca ttt aga gat cct gct gtt tgg cca ccc cct         402
Ser Cys Gln Asp Glu Pro Phe Arg Asp Pro Ala Val Trp Pro Pro Pro
```

-continued

|  |  |  |  | 90 |  |  |  | 95 |  |  |  | 100 |  |  |  |  |
|---|---|---|---|---|---|---|---|---|---|---|---|---|---|---|---|---|
| gta | cct | gca | gaa | cac | aga | gct | cca | cct | cag | ata | agg | cgt | ccc | aat | cga | 450 |
| Val | Pro | Ala | Glu | His | Arg | Ala | Pro | Pro | Gln | Ile | Arg | Arg | Pro | Asn | Arg |  |
|  |  | 105 |  |  |  |  | 110 |  |  |  |  | 115 |  |  |  |  |
| gaa | gta | aga | cct | ctg | agg | aaa | gaa | atg | cca | gga | gta | gga | gcc | cgg | gga | 498 |
| Glu | Val | Arg | Pro | Leu | Arg | Lys | Glu | Met | Pro | Gly | Val | Gly | Ala | Arg | Gly |  |
| 120 |  |  |  |  | 125 |  |  |  |  | 130 |  |  |  |  |  |  |
| cct | gta | ggc | cga | gca | cat | cct | ata | tca | aag | ggt | gaa | aaa | ccc | tct | aca | 546 |
| Pro | Val | Gly | Arg | Ala | His | Pro | Ile | Ser | Lys | Gly | Glu | Lys | Pro | Ser | Thr |  |
| 135 |  |  |  |  | 140 |  |  |  |  | 145 |  |  |  |  | 150 |  |
| agt | aga | gac | aag | gat | tat | aga | gca | aga | gga | aga | gat | gat | aag | gga | agg | 594 |
| Ser | Arg | Asp | Lys | Asp | Tyr | Arg | Ala | Arg | Gly | Arg | Asp | Asp | Lys | Gly | Arg |  |
|  |  |  |  | 155 |  |  |  |  | 160 |  |  |  |  | 165 |  |  |
| aag | aat | atg | cat | gat | ggt | gcg | agc | gat | ggt | gaa | att | cct | aaa | ttt | gat | 642 |
| Lys | Asn | Met | His | Asp | Gly | Ala | Ser | Asp | Gly | Glu | Ile | Pro | Lys | Phe | Asp |  |
|  |  |  | 170 |  |  |  |  | 175 |  |  |  |  | 180 |  |  |  |
| ggt | gct | ggg | tat | gat | aag | gat | ctg | gtg | gaa | gcc | ctg | gag | aga | gac | att | 690 |
| Gly | Ala | Gly | Tyr | Asp | Lys | Asp | Leu | Val | Glu | Ala | Leu | Glu | Arg | Asp | Ile |  |
|  |  | 185 |  |  |  |  | 190 |  |  |  |  | 195 |  |  |  |  |
| gta | tcc | agg | aat | ccc | agc | att | cat | tgg | gat | gac | ata | gca | gat | ctg | gaa | 738 |
| Val | Ser | Arg | Asn | Pro | Ser | Ile | His | Trp | Asp | Asp | Ile | Ala | Asp | Leu | Glu |  |
| 200 |  |  |  |  | 205 |  |  |  |  | 210 |  |  |  |  |  |  |
| gaa | gct | aag | aag | ttg | cta | agg | gaa | gct | gtt | gtt | ctt | cca | atg | tgg | atg | 786 |
| Glu | Ala | Lys | Lys | Leu | Leu | Arg | Glu | Ala | Val | Val | Leu | Pro | Met | Trp | Met |  |
| 215 |  |  |  |  | 220 |  |  |  |  | 225 |  |  |  |  | 230 |  |
| cct | gac | ttt | ttc | aaa | ggg | att | aga | agg | cca | tgg | aag | ggt | gta | ctg | atg | 834 |
| Pro | Asp | Phe | Phe | Lys | Gly | Ile | Arg | Arg | Pro | Trp | Lys | Gly | Val | Leu | Met |  |
|  |  |  |  | 235 |  |  |  |  | 240 |  |  |  |  | 245 |  |  |
| gtt | gga | ccc | ccg | ggc | act | ggt | aag | act | atg | cta | gct | aaa | gct | gtt | gcc | 882 |
| Val | Gly | Pro | Pro | Gly | Thr | Gly | Lys | Thr | Met | Leu | Ala | Lys | Ala | Val | Ala |  |
|  |  |  | 250 |  |  |  |  | 255 |  |  |  |  | 260 |  |  |  |
| act | gaa | tgt | ggc | aca | aca | ttc | ttc | aat | gtt | tca | tct | tct | aca | ctg | aca | 930 |
| Thr | Glu | Cys | Gly | Thr | Thr | Phe | Phe | Asn | Val | Ser | Ser | Ser | Thr | Leu | Thr |  |
|  |  | 265 |  |  |  |  | 270 |  |  |  |  | 275 |  |  |  |  |
| tct | aaa | tat | aga | ggt | gaa | tct | gag | aag | tta | gtc | cgt | ctg | ttg | ttt | gaa | 978 |
| Ser | Lys | Tyr | Arg | Gly | Glu | Ser | Glu | Lys | Leu | Val | Arg | Leu | Leu | Phe | Glu |  |
| 280 |  |  |  |  | 285 |  |  |  |  | 290 |  |  |  |  |  |  |
| atg | gct | aga | ttt | tat | gcg | ccc | act | acg | atc | ttc | atc | gat | gaa | ata | gat | 1026 |
| Met | Ala | Arg | Phe | Tyr | Ala | Pro | Thr | Thr | Ile | Phe | Ile | Asp | Glu | Ile | Asp |  |
| 295 |  |  |  |  | 300 |  |  |  |  | 305 |  |  |  |  | 310 |  |
| tct | atc | tgt | agt | cga | aga | gga | acc | tca | gat | gaa | cat | gag | gca | agt | cgc | 1074 |
| Ser | Ile | Cys | Ser | Arg | Arg | Gly | Thr | Ser | Asp | Glu | His | Glu | Ala | Ser | Arg |  |
|  |  |  |  | 315 |  |  |  |  | 320 |  |  |  |  | 325 |  |  |
| aga | gtc | aag | tct | gaa | cta | ctc | att | cag | atg | gat | gga | gtt | gga | gga | gct | 1122 |
| Arg | Val | Lys | Ser | Glu | Leu | Leu | Ile | Gln | Met | Asp | Gly | Val | Gly | Gly | Ala |  |
|  |  |  | 330 |  |  |  |  | 335 |  |  |  |  | 340 |  |  |  |
| tta | gag | aat | gat | gat | cct | tcc | aaa | atg | gtt | atg | gta | ttg | gcc | gct | act | 1170 |
| Leu | Glu | Asn | Asp | Asp | Pro | Ser | Lys | Met | Val | Met | Val | Leu | Ala | Ala | Thr |  |
|  |  | 345 |  |  |  |  | 350 |  |  |  |  | 355 |  |  |  |  |
| aat | ttc | cca | tgg | gac | att | gat | gaa | gct | ttg | aga | agg | aga | tta | gaa | aag | 1218 |
| Asn | Phe | Pro | Trp | Asp | Ile | Asp | Glu | Ala | Leu | Arg | Arg | Arg | Leu | Glu | Lys |  |
| 360 |  |  |  |  | 365 |  |  |  |  | 370 |  |  |  |  |  |  |
| agg | ata | tat | ata | cct | ctc | cca | aca | gca | aaa | gga | aga | act | gag | ctg | ctg | 1266 |
| Arg | Ile | Tyr | Ile | Pro | Leu | Pro | Thr | Ala | Lys | Gly | Arg | Thr | Glu | Leu | Leu |  |
| 375 |  |  |  |  | 380 |  |  |  |  | 385 |  |  |  |  | 390 |  |
| aag | att | aat | ctt | cgt | gaa | gtt | gaa | ctg | gat | cct | gac | att | caa | ctg | gaa | 1314 |
| Lys | Ile | Asn | Leu | Arg | Glu | Val | Glu | Leu | Asp | Pro | Asp | Ile | Gln | Leu | Glu |  |
|  |  |  |  | 395 |  |  |  |  | 400 |  |  |  |  | 405 |  |  |
| gat | ata | gca | gag | aag | ata | gag | ggc | tat | tct | ggt | gct | gat | ata | act | aat | 1362 |

```
Asp Ile Ala Glu Lys Ile Glu Gly Tyr Ser Gly Ala Asp Ile Thr Asn
            410                 415                 420 gtt tgc agg gat gcc tct tta atg gca atg aga cgg cga atc aat ggc      1410
Val Cys Arg Asp Ala Ser Leu Met Ala Met Arg Arg Arg Ile Asn Gly
        425                 430                 435 tta ggt cca gaa gag atc cgt gca ctt tct aaa gag gaa ctt cag atg      1458
Leu Gly Pro Glu Glu Ile Arg Ala Leu Ser Lys Glu Glu Leu Gln Met
440                 445                 450 cct gtt acc aaa gga gac ttt gaa ttg gct ctt aag aaa att gct aag      1506
Pro Val Thr Lys Gly Asp Phe Glu Leu Ala Leu Lys Lys Ile Ala Lys
455                 460                 465                 470 tct gtc tct gct gca gac ttg gag aag tat gaa aaa tgg atg gtc gaa      1554
Ser Val Ser Ala Ala Asp Leu Glu Lys Tyr Glu Lys Trp Met Val Glu
                475                 480                 485 ttt gga tct gct tga atttctgtca gctctttcat ttctggtatt tttatttata    1609
Phe Gly Ser Ala
            490 aaatgtgaag aaattccctg caattttttt aaaaaaacaa gtttagaact tttcattgga   1669 gagactttc ccttaaagga aaaaacctaa aaccacaaag aatataaata tagctgggaa    1729 agaagaaaag cttacatagg gagcctgata g                                 1760

<210> SEQ ID NO 2
<211> LENGTH: 490
<212> TYPE: PRT
<213> ORGANISM: Canis familiaris

<400> SEQUENCE: 2

Met Asn Leu Ala Glu Ile Cys Asp Asn Ala Lys Lys Gly Arg Glu Tyr
1               5                   10                  15

Ala Leu Leu Gly Asn Tyr Asp Ser Ser Met Val Tyr Tyr Gln Gly Val
            20                  25                  30

Ile Gln Gln Ile Gln Arg His Cys Gln Ser Val Arg Asp Pro Ala Val
        35                  40                  45

Lys Gly Lys Trp Gln Gln Val Arg Gln Glu Leu Leu Glu Glu Tyr Glu
    50                  55                  60

Gln Val Lys Asn Ile Val Ser Thr Leu Glu Ser Phe Lys Met Asp Lys
65                  70                  75                  80

Pro Pro Asp Phe Pro Val Ser Cys Gln Asp Glu Pro Phe Arg Asp Pro
                85                  90                  95

Ala Val Trp Pro Pro Val Pro Ala Glu His Arg Ala Pro Pro Gln
            100                 105                 110

Ile Arg Arg Pro Asn Arg Glu Val Arg Pro Leu Arg Lys Glu Met Pro
        115                 120                 125

Gly Val Gly Ala Arg Gly Pro Val Gly Arg Ala His Pro Ile Ser Lys
    130                 135                 140

Gly Glu Lys Pro Ser Thr Ser Arg Asp Lys Asp Tyr Arg Ala Arg Gly
145                 150                 155                 160

Arg Asp Asp Lys Gly Arg Lys Asn Met His Asp Gly Ala Ser Asp Gly
                165                 170                 175

Glu Ile Pro Lys Phe Asp Gly Ala Gly Tyr Asp Lys Asp Leu Val Glu
            180                 185                 190

Ala Leu Glu Arg Asp Ile Val Ser Arg Asn Pro Ser Ile His Trp Asp
        195                 200                 205

Asp Ile Ala Asp Leu Glu Glu Ala Lys Lys Leu Leu Arg Glu Ala Val
    210                 215                 220
```

```
Val Leu Pro Met Trp Met Pro Asp Phe Phe Lys Gly Ile Arg Arg Pro
225                 230                 235                 240

Trp Lys Gly Val Leu Met Val Gly Pro Pro Gly Thr Gly Lys Thr Met
            245                 250                 255

Leu Ala Lys Ala Val Ala Thr Glu Cys Gly Thr Thr Phe Phe Asn Val
        260                 265                 270

Ser Ser Ser Thr Leu Thr Ser Lys Tyr Arg Gly Glu Ser Glu Lys Leu
    275                 280                 285

Val Arg Leu Leu Phe Glu Met Ala Arg Phe Tyr Ala Pro Thr Thr Ile
290                 295                 300

Phe Ile Asp Glu Ile Asp Ser Ile Cys Ser Arg Arg Gly Thr Ser Asp
305                 310                 315                 320

Glu His Glu Ala Ser Arg Arg Val Lys Ser Glu Leu Leu Ile Gln Met
            325                 330                 335

Asp Gly Val Gly Gly Ala Leu Glu Asn Asp Asp Pro Ser Lys Met Val
        340                 345                 350

Met Val Leu Ala Ala Thr Asn Phe Pro Trp Asp Ile Asp Glu Ala Leu
    355                 360                 365

Arg Arg Arg Leu Glu Lys Arg Ile Tyr Ile Pro Leu Pro Thr Ala Lys
370                 375                 380

Gly Arg Thr Glu Leu Leu Lys Ile Asn Leu Arg Glu Val Glu Leu Asp
385                 390                 395                 400

Pro Asp Ile Gln Leu Glu Asp Ile Ala Glu Lys Ile Glu Gly Tyr Ser
            405                 410                 415

Gly Ala Asp Ile Thr Asn Val Cys Arg Asp Ala Ser Leu Met Ala Met
        420                 425                 430

Arg Arg Arg Ile Asn Gly Leu Gly Pro Glu Glu Ile Arg Ala Leu Ser
    435                 440                 445

Lys Glu Glu Leu Gln Met Pro Val Thr Lys Gly Asp Phe Glu Leu Ala
450                 455                 460

Leu Lys Lys Ile Ala Lys Ser Val Ser Ala Ala Asp Leu Glu Lys Tyr
465                 470                 475                 480

Glu Lys Trp Met Val Glu Phe Gly Ser Ala
            485                 490

<210> SEQ ID NO 3
<211> LENGTH: 7536
<212> TYPE: DNA
<213> ORGANISM: Homo sapiens
<220> FEATURE:
<221> NAME/KEY: CDS
<222> LOCATION: (132)..(1604)
<223> OTHER INFORMATION:

<400> SEQUENCE: 3
ccttttcacg cgcgtcgcga gctaacggac tcggcggcgg cggcggcggc ggcctgcgcc      60
ccacccgcac cccatctgga ccgcatcgct gaatgtgccc ggacctgcgc cttctgggtc     120
tctgaaagaa g atg aat ttg gct gag att tgt gat aat gca aag aaa gga     170
            Met Asn Leu Ala Glu Ile Cys Asp Asn Ala Lys Lys Gly
            1               5                   10 aga gaa tat gcc ctt ctt gga aat tac gac tca tca atg gta tat tac     218
Arg Glu Tyr Ala Leu Leu Gly Asn Tyr Asp Ser Ser Met Val Tyr Tyr
        15                  20                  25 cag ggg gtg atg cag cag att cag aga cat tgc cag tca gtc aga gat     266
Gln Gly Val Met Gln Gln Ile Gln Arg His Cys Gln Ser Val Arg Asp
30                  35                  40                  45
```

| | | |
|---|---|---|
| cca gct atc aaa ggc aaa tgg caa cag gtt cgg cag gaa tta ttg gag<br>Pro Ala Ile Lys Gly Lys Trp Gln Gln Val Arg Gln Glu Leu Leu Glu<br>50 55 60 | | 314 |
| gaa tat gaa caa gtt aaa agt att gtc agc act tta gaa agt ttt aaa<br>Glu Tyr Glu Gln Val Lys Ser Ile Val Ser Thr Leu Glu Ser Phe Lys<br>65 70 75 | | 362 |
| att gac aag cct cca gat ttc cct gtg tcc tgt caa gat gaa cca ttt<br>Ile Asp Lys Pro Pro Asp Phe Pro Val Ser Cys Gln Asp Glu Pro Phe<br>80 85 90 | | 410 |
| aga gat cct gct gtt tgg cca ccc cct gtt cct gca gaa cac aga gct<br>Arg Asp Pro Ala Val Trp Pro Pro Pro Val Pro Ala Glu His Arg Ala<br>95 100 105 | | 458 |
| cca cct cag atc agg cgt ccc aat cga gaa gta aga cct ctg agg aaa<br>Pro Pro Gln Ile Arg Arg Pro Asn Arg Glu Val Arg Pro Leu Arg Lys<br>110 115 120 125 | | 506 |
| gaa atg gca gga gta gga gcc cgg gga cct gta ggc cga gca cat cct<br>Glu Met Ala Gly Val Gly Ala Arg Gly Pro Val Gly Arg Ala His Pro<br>130 135 140 | | 554 |
| ata tca aag agt gaa aag cct tct aca agt agg gac aag gac tat aga<br>Ile Ser Lys Ser Glu Lys Pro Ser Thr Ser Arg Asp Lys Asp Tyr Arg<br>145 150 155 | | 602 |
| gca aga ggg aga gat gac aag gga agg aag aat atg caa gat ggt gca<br>Ala Arg Gly Arg Asp Asp Lys Gly Arg Lys Asn Met Gln Asp Gly Ala<br>160 165 170 | | 650 |
| agt gat ggt gaa atg cca aaa ttt gat ggt gct ggt tat gat aag gat<br>Ser Asp Gly Glu Met Pro Lys Phe Asp Gly Ala Gly Tyr Asp Lys Asp<br>175 180 185 | | 698 |
| ctg gtg gaa gcc ctt gaa aga gac att gta tcc agg aat cct agc att<br>Leu Val Glu Ala Leu Glu Arg Asp Ile Val Ser Arg Asn Pro Ser Ile<br>190 195 200 205 | | 746 |
| cat tgg gat gac ata gca gat ctg gaa gaa gct aag aag ttg cta agg<br>His Trp Asp Asp Ile Ala Asp Leu Glu Glu Ala Lys Lys Leu Leu Arg<br>210 215 220 | | 794 |
| gaa gct gtt gtt ctt cca atg tgg atg cct gac ttt ttc aaa ggg att<br>Glu Ala Val Val Leu Pro Met Trp Met Pro Asp Phe Phe Lys Gly Ile<br>225 230 235 | | 842 |
| aga agg cca tgg aag ggt gta ctg atg gtt gga ccc cca ggc act ggt<br>Arg Arg Pro Trp Lys Gly Val Leu Met Val Gly Pro Pro Gly Thr Gly<br>240 245 250 | | 890 |
| aaa act atg cta gct aaa gct gtt gcc act gaa tgt ggt aca aca ttc<br>Lys Thr Met Leu Ala Lys Ala Val Ala Thr Glu Cys Gly Thr Thr Phe<br>255 260 265 | | 938 |
| ttc aac gtt tcg tct tct aca ctg aca tct aaa tac aga ggt gaa tct<br>Phe Asn Val Ser Ser Ser Thr Leu Thr Ser Lys Tyr Arg Gly Glu Ser<br>270 275 280 285 | | 986 |
| gag aag tta gtt cgt ctg ttg ttt gag atg gct aga ttt tat gcc cct<br>Glu Lys Leu Val Arg Leu Leu Phe Glu Met Ala Arg Phe Tyr Ala Pro<br>290 295 300 | | 1034 |
| acc acg atc ttc att gat gag ata gat tct atc tgc agt cga aga gga<br>Thr Thr Ile Phe Ile Asp Glu Ile Asp Ser Ile Cys Ser Arg Arg Gly<br>305 310 315 | | 1082 |
| acc tct gat gaa cat gag gca agt cgc agg gtc aag tct gaa ctg ctc<br>Thr Ser Asp Glu His Glu Ala Ser Arg Arg Val Lys Ser Glu Leu Leu<br>320 325 330 | | 1130 |
| att cag atg gat gga gtt gga gga gct tta gaa aat gat gat cct tcc<br>Ile Gln Met Asp Gly Val Gly Gly Ala Leu Glu Asn Asp Asp Pro Ser<br>335 340 345 | | 1178 |
| aaa atg gtt atg gta ttg gct gct act aat ttc ccg tgg gac att gat<br>Lys Met Val Met Val Leu Ala Ala Thr Asn Phe Pro Trp Asp Ile Asp<br>350 355 360 365 | | 1226 |

```
gaa gct ttg cga aga agg tta gaa aaa agg ata tat ata cct ctc cca      1274
Glu Ala Leu Arg Arg Arg Leu Glu Lys Arg Ile Tyr Ile Pro Leu Pro
                370                 375                 380 aca gca aaa gga aga gct gag ctt ctg aag atc aac ctt cgt gag gtc      1322
Thr Ala Lys Gly Arg Ala Glu Leu Leu Lys Ile Asn Leu Arg Glu Val
            385                 390                 395 gaa tta gat cct gat att caa ctg gaa gat ata gcc gag aag att gag      1370
Glu Leu Asp Pro Asp Ile Gln Leu Glu Asp Ile Ala Glu Lys Ile Glu
        400                 405                 410 ggc tat tct ggt gct gac atc act aat gtt tgc agg gat gcc tct tta      1418
Gly Tyr Ser Gly Ala Asp Ile Thr Asn Val Cys Arg Asp Ala Ser Leu
    415                 420                 425 atg gca atg aga cgg cgt atc aat ggc tta agt cca gaa gaa atc cgt      1466
Met Ala Met Arg Arg Arg Ile Asn Gly Leu Ser Pro Glu Glu Ile Arg
430                 435                 440                 445 gca ctt tct aaa gag gaa ctt cag atg cct gtt acc aaa gga gac ttt      1514
Ala Leu Ser Lys Glu Glu Leu Gln Met Pro Val Thr Lys Gly Asp Phe
                450                 455                 460 gaa ttg gcc cta aag aaa att gct aag tct gtc tct gct gca gac ttg      1562
Glu Leu Ala Leu Lys Lys Ile Ala Lys Ser Val Ser Ala Ala Asp Leu
            465                 470                 475 gag aag tat gaa aaa tgg atg gtt gaa ttt gga tct gct tga              1604
Glu Lys Tyr Glu Lys Trp Met Val Glu Phe Gly Ser Ala
        480                 485                 490 atttctgtca gctctttaat ttctggtatt tttgttgata aaatacgaag aaattcctgc    1664 aattttaaa aaacaagttt ggaattttt tcagtggagt ggttttcgct taaaggaaaa      1724
aaaaatctaa aactgcgaag aatactaaat gtagttgaga ataattgat ggcgagagtt    1784 tgctagtctc cctccccggc tttgtgctgg tattccacgt attcctgcat taatattgca    1844
cacccaaacc agtctatcag ggaggctgaa gcaagggcgc agtgtgatat tttaggaata    1904
cagaagattt agaaataccc ctatttctca tttgcagttt ttttttccaa ttctgtgctc    1964
tgtcaacatg agggacctat ctatgtatgt tgacttttaa catcaaaatt ggatttgtgt    2024
caaacattca ttgttaagag aagaatgaca gtatatttg gaggaaataa tgaatttact    2084
aattaaacct ttagaattta tgacttactg ttagagtctg tcatatggtt agaattttta    2144
cttccgctac ccctgccatt tcttctgcta gctacttcat aatatcttga gctttactga    2204
ggaatattct cacgctctgt ggtatttgaa tcattttgcc aggtcatttc tctgtcttta    2264
gtattttttg ctggtgcttc ttacatttaa tatggaaagg tgggaagaat attactgcat    2324
tagatgtaat tcttcattct agacttccaa gtttgttttc acttttttgt gtgtgcgtga    2384
aggagtctgt gtcacccagg ctgtgtagtg cagtggttga tcttggctca ctgcaacctc    2444
tgcctcctag attcaagcaa ttctcctgtc tcagcctccc aagtagctgg gattacaggt    2504
gcgcaccacc atgcctggct gtgttttcac ttttctttca acatgttcaa ccagatatat    2564
agccattatt tttctcagct ccagcattgt ttgattttc ttgagtttga ttttagtatt    2624
tgagataaat acttttacat tctaaacaag tccactctct gtggctaacg caaaacaaat    2684
gaaatcttta ttgttttcca aacagctagt ttaacaaaac agcatcatac atagtgaatg    2744
atgttcattg gaaaattcta aaatttgtcc ttgtctaggt tgagaacttt tacacacact    2804
aagataaaga tagaaatctg acatgctcac tcaattcagc aggaattaca cattagaaag    2864
aagccagaaa aataaatggc atatatccaa tcacaagtaa atgatcctgg cgttagtttt    2924
tatgattaca tgtgtctcat taggcaattt atgctttaat ggtcaagctt ttaaaaattt    2984
```

```
gtatttgata acatcctgaa ttctcagttt cgaatagtgc ctactggttt aaaactaaaa   3044
ataatacagc ttttttggaca tttaaccaag atactaagaa ggttttttttt aaaaaaagag  3104 atttgattat ttttcccctgc taaaaactgt aaatgcctta tgttcttttc agataactta   3164
agtctgacct aaactccagt attcatctga tgctgtaaat tgcccttctt tctgagacac    3224
agattataag atgccagatc ataagacatc atgattttat tgtaattgaa ttcttcctaa   3284
aaattgagag gtttcctttt attaactttt aaaataaaga aataagtagt ttcattacga   3344
ttattttgca aactattgcc agtcagaaat gcactttttt tttccctgaa gttttaggag    3404
ccgtcactaa aacattagtc ttgtgattgt taaaacttgt ttgtaatggg ttggtgcaaa    3464
agtaattgtg gttttttccat tactttcaat ggcaaaaacc gcaattactt ttgcaccagc   3524
ctaacaatag ttgattagtt agacctttttc tgggttttgt attgattatc ttggtgtgca   3584
tttaattatt tttctgaatt cttcatggat aatgacatag taattgtgat tcttttaata   3644
ccagttaagc agtatttggc aacttaaact tcctgggagc ctaactttac tatgttaagt   3704
gagtcaggtg tgcttttttat ttcccttgtt tctcattttg ccctgtcagt ggatggtaga   3764
tgctttgtat atcttaaatc ccttaaagga tcttaaagac atccctcagg tgttctattt    3824
aacttttatt ttattttatt ttatttattt atttattttg agactgagtc ttgctctgtc    3884
gcccaggctg gagtgcagtg gcatgatctc ggctcactgc aacttctgcc tcccaggttc    3944
aagccattct cctgcctcgg cctcctgagt agctgggatt acagttgccg ccacacccgg    4004 cttattttttt tgtatttttta gtagaggcag agtttcacca tgttggccag gctagtctcg    4064
aactcctgac ctcagatgat ccgcccacat tggcctccca aagtgctggg attacaggtg    4124
tgatccaccg cacctggccc taacttttaa tatacaacac acacacacac acacacacac    4184
acacacacac acacacacac acacacacac acactatttc agaagacagt gtgttgcctt    4244
acccagaatg agtgctagga ttacaggcgt gagacagaca cacatacaca cacatacaca    4304
cacacagagt ctttattgca gaagacagtg tgttgcctta taggcgtgag acacacacac    4364
acacacacac acacacacac acacacacag tctttattgc agaagacagt gtgttgcctt    4424
accagaatga gtgcttggat tacaggcgtg agccactgtg cccagcccta acttttaatg    4484
tacatcacac acacactcac actcacatac acacacacac acacactctg actgtcttta    4544
ttgcagaaga cagtgtgttg ccttacccag aatgagattg aattgttttg cttcgttttg    4604
ttttgttatt cagtgttgcg gtagcagatg cattatcaaa ggaaaaatat ttggctcctt   4664
taattcctct gaaaacatga gtattttgag ttctgcagca caatgactgt aggactaagc    4724
taagtctgct ttgcagatat ctgatcagat agtcccttca ttctgtagac gtgtattggt    4784
tggtccaaga cacagtgagt aggagctctg tggaccaaga caaagctgga ctagagagta    4844
cagttcaaac ttggcagttt ctctaacgac tctgtatagc ttctggcttc tactactgaa    4904
acaagagttt agatcactga tggagaggca tagtaatctg tttgtgcttt ggaaaaatat    4964
ataaaagttt ttttcccccta tttttttgcac tttaaatctg ttttgaaatt agaactgata   5024
tacatttatt tgaataatgt gtaactatta tggatctatt ttaatgaaca atttttacca    5084
tttcccaagc tgcctgtttta ttataagcat gacatgttta ctataaacct tttgcccccca   5144 taatttcttt ttttaaagga aattaatatt agtaaaataa acacctcttt aatggaagct    5204
gcaaccttct agtgatccaa gtagacaata gatggtggca tcacagactt tatctacaca    5264 cttcttcgggtc tgaccactac ctcccacaat acctagccat tttggaaggg gaaaacatgc    5324
ggtggtctag ctgtatagct cagggcttaa tttcagcttc tgagattgtg atgtcatatt    5384
```

```
tcactctcaa acataggct gaaagcacga attactcaaa aagtaagcaa accaatacct    5444
ggtgaatcta tggacagtca tacacataca tcaggggaaa atgtgtgtgt acaacccaaa    5504
tttacagtat gattgtcatt ctttgacttt gttttgtata gcctgactct gttgaacatg    5564
aaattattag tactctaggt tttggacagc ttgagttcat ttgaattcct tccttaggaa    5624
taagttttta tatacactgc taaatgtgtg atgagaatca taaaacacta accagctgag    5684
gtagctgtga ttcactttcc ccccacccta acttgagata aaatgaagga ctaggcaagt    5744
atttcatgtt gtgtgagtgg acttcggttc cttcagtatt gtctaggtta ttgagtcttt    5804 cttttgcctaa tagtggattc ccactcttaa gataactttt attagtgata aatcagttta    5864
gggtatattc tgtatgacag gcataaaatg ttaagggtga atgctggcct tttccaagaa    5924
aaggccacct taacttgtat gaggaaaaaa tcctaactat tctctttttt gtatcttttt    5984
ttccgtaact gttttgattg tatattttaa agaaaccact taatttgtga tgcacgtaat    6044
atttgtgtga acctgagaat atgtcacaat aggaaaaagc agaaattata cttaggggac    6104
atgttagggg ggtaaaaata tttaagcctc gaatgtttta ctgtcatctc cactaactat    6164
ttttacagaa aaagctaaaa actctgttgt aattattgta agtttactta tttatacttt    6224
taaattaggc ttttcatact taaattttttt tgacatttgc ttttaatatt tgtttcttaa    6284
tgtggaaatt gtgtatttta ataatcaaat tattaggata atagatatat ttttaaacat    6344
tcacctcatt aacaaataga tctttgaatt tttattaggt tttttggctc cagacaactg    6404
tttagcttta atgatatttc taaattccca gtgacttatt aataaaaaca ggaaaaatat    6464
ttaggtaatg tcataaaatt tatttttaccct ttctcatttt ctgagaaaat aaatgaaaaa    6524
aaccctagat attgctttat taccaacagt gtgtaggttt ttgtacatat ggaaatttga    6584
cacaaaaaaa tagggaattt gtatagagaa gtttccctct tataaaagga ctcccatttg    6644
attgttcgaa actataaaat gcacttttac tttaccatat ctgaaatgac aaaatatcgc    6704
cctttggaaa acctgactct ttgcacgtgt aattcccaga gtctacctca gttaaccagg    6764
cttagtttta ggcaggaatg aattgaatta aattcagttc atcatctatg cagatttgtt    6824
tcttttaagc acatccttcc ctcctgctgt tgccctcctc ccattaactt ttcttttttaa    6884 tcttgaaatt gttttaaaata ttccatctttt cttttctctag caaagtgttt gtattccaaa    6944
taaggcctct gtgaaatgtc tgaattactt ttcccgtctt tgttatggtc agcttcatta    7004
tttggatgta ttgcattcaa agcagcagtt ccaaacataa cacacatcta ttttcttaga    7064
gttttgtaaa tacaaactaa cctgatgaca ttaaaaattg tggatcctac atgttcctat    7124
gttcattctc taaaaccctg agtaacttta tgaaaacaca caaacctgga aaaacatcac    7184 attttttgtca catttttact gacaaatgta tattcatatg atggtacggc agcagggagt    7244 ggccccccagt taacatggct gtgagtggac acagtgtctc gcaggatcac tgcatgttat    7304
gatggcttgt aagtgcgttg ttaagacttt tgtttcagtg ttttgtctccc agtatttgaa    7364 cctaatttaa agaaaaagac gtttccaagt tgtatttatt aaatgtgttt ttccttacct    7424
tttgtgctgc tactttgcta atctcattag cttagctgtg tttgtgcata ggttatatttt    7484 ggtaataaat ttatagagtg ttggttgtca aaaaaaaaaa aaaaaaaaaa aa             7536
```

<210> SEQ ID NO 4
<211> LENGTH: 490
<212> TYPE: PRT
<213> ORGANISM: Homo sapiens

<400> SEQUENCE: 4

```
Met Asn Leu Ala Glu Ile Cys Asp Asn Ala Lys Lys Gly Arg Glu Tyr
1               5                   10                  15

Ala Leu Leu Gly Asn Tyr Asp Ser Ser Met Val Tyr Gln Gly Val
            20                  25                  30

Met Gln Gln Ile Gln Arg His Cys Gln Ser Val Arg Asp Pro Ala Ile
            35                  40                  45

Lys Gly Lys Trp Gln Gln Val Arg Gln Glu Leu Leu Glu Glu Tyr Glu
50                  55                  60

Gln Val Lys Ser Ile Val Ser Thr Leu Glu Ser Phe Lys Ile Asp Lys
65                  70                  75                  80

Pro Pro Asp Phe Pro Val Ser Cys Gln Asp Glu Pro Phe Arg Asp Pro
                85                  90                  95

Ala Val Trp Pro Pro Val Pro Ala Glu His Arg Ala Pro Pro Gln
            100                 105                 110

Ile Arg Arg Pro Asn Arg Glu Val Arg Pro Leu Arg Lys Glu Met Ala
            115                 120                 125

Gly Val Gly Ala Arg Gly Pro Val Gly Arg Ala His Pro Ile Ser Lys
130                 135                 140

Ser Glu Lys Pro Ser Thr Ser Arg Asp Lys Asp Tyr Arg Ala Arg Gly
145                 150                 155                 160

Arg Asp Asp Lys Gly Arg Lys Asn Met Gln Asp Gly Ala Ser Asp Gly
                165                 170                 175

Glu Met Pro Lys Phe Asp Gly Ala Gly Tyr Asp Lys Asp Leu Val Glu
            180                 185                 190

Ala Leu Glu Arg Asp Ile Val Ser Arg Asn Pro Ser Ile His Trp Asp
            195                 200                 205

Asp Ile Ala Asp Leu Glu Glu Ala Lys Lys Leu Leu Arg Glu Ala Val
210                 215                 220

Val Leu Pro Met Trp Met Pro Asp Phe Phe Lys Gly Ile Arg Arg Pro
225                 230                 235                 240

Trp Lys Gly Val Leu Met Val Gly Pro Pro Gly Thr Gly Lys Thr Met
                245                 250                 255

Leu Ala Lys Ala Val Ala Thr Glu Cys Gly Thr Thr Phe Phe Asn Val
            260                 265                 270

Ser Ser Ser Thr Leu Thr Ser Lys Tyr Arg Gly Glu Ser Glu Lys Leu
            275                 280                 285

Val Arg Leu Leu Phe Glu Met Ala Arg Phe Tyr Ala Pro Thr Thr Ile
290                 295                 300

Phe Ile Asp Glu Ile Asp Ser Ile Cys Ser Arg Arg Gly Thr Ser Asp
305                 310                 315                 320

Glu His Glu Ala Ser Arg Arg Val Lys Ser Glu Leu Leu Ile Gln Met
                325                 330                 335

Asp Gly Val Gly Gly Ala Leu Glu Asn Asp Asp Pro Ser Lys Met Val
            340                 345                 350

Met Val Leu Ala Ala Thr Asn Phe Pro Trp Asp Ile Asp Glu Ala Leu
            355                 360                 365

Arg Arg Arg Leu Glu Lys Arg Ile Tyr Ile Pro Leu Pro Thr Ala Lys
370                 375                 380

Gly Arg Ala Glu Leu Leu Lys Ile Asn Leu Arg Glu Val Glu Leu Asp
385                 390                 395                 400

Pro Asp Ile Gln Leu Glu Asp Ile Ala Glu Lys Ile Glu Gly Tyr Ser
                405                 410                 415
```

```
Gly Ala Asp Ile Thr Asn Val Cys Arg Asp Ala Ser Leu Met Ala Met
            420                 425                 430

Arg Arg Arg Ile Asn Gly Leu Ser Pro Glu Glu Ile Arg Ala Leu Ser
            435                 440                 445

Lys Glu Glu Leu Gln Met Pro Val Thr Lys Gly Asp Phe Glu Leu Ala
450                 455                 460

Leu Lys Lys Ile Ala Lys Ser Val Ser Ala Ala Asp Leu Glu Lys Tyr
465                 470                 475                 480

Glu Lys Trp Met Val Glu Phe Gly Ser Ala
            485                 490

<210> SEQ ID NO 5
<211> LENGTH: 6173
<212> TYPE: DNA
<213> ORGANISM: Mus musculus
<220> FEATURE:
<221> NAME/KEY: CDS
<222> LOCATION: (137)..(1603)
<223> OTHER INFORMATION:

<400> SEQUENCE: 5
```

| | | |
|---|---|---|
| agcgcggcga cagactgata aattgggagc tactcagatg gtgttaaagt gactctttgt | 60 |
| ctgcaggggg ctccggggtg gtcgctggat tgggcgctgt gcgtcgggcg ggggtagcgc | 120 |
| aggtgtctga aagaag atg aat ttg gcg gag att tgt gag aat gcg aag aaa | 172 |
|  Met Asn Leu Ala Glu Ile Cys Glu Asn Ala Lys Lys | |
|   1               5                  10          | |
| ggc cgg gaa tat gcg ctt ctg gga aat tat gac tcg tca atg gtg tat | 220 |
| Gly Arg Glu Tyr Ala Leu Leu Gly Asn Tyr Asp Ser Ser Met Val Tyr | |
|         15                 20                 25                | |
| tac cag gga gtg ata cag cag atc cag aga cac tgc cag tca ctg aga | 268 |
| Tyr Gln Gly Val Ile Gln Gln Ile Gln Arg His Cys Gln Ser Leu Arg | |
|     30                 35                 40                    | |
| gac ccg gcc acc aaa gcc aag tgg cag cag gta cgg cag gaa ctc ttg | 316 |
| Asp Pro Ala Thr Lys Ala Lys Trp Gln Gln Val Arg Gln Glu Leu Leu | |
| 45                 50                 55                 60     | |
| gaa gaa tat gaa cag gtt aag agt atc gtc agc act tta gaa agc ttt | 364 |
| Glu Glu Tyr Glu Gln Val Lys Ser Ile Val Ser Thr Leu Glu Ser Phe | |
|             65                 70                 75            | |
| aag atg gac aag ccc cct gac ttc ccc gtg tct tgc cga gat gaa ccg | 412 |
| Lys Met Asp Lys Pro Pro Asp Phe Pro Val Ser Cys Arg Asp Glu Pro | |
|         80                 85                 90                | |
| ttt aga gac cct gca gta tgg cca ccc cct gtc cct gcg gaa cac aga | 460 |
| Phe Arg Asp Pro Ala Val Trp Pro Pro Pro Val Pro Ala Glu His Arg | |
|     95                 100                105                   | |
| gca ccc cct caa atc agg cgt cca aat cgc gaa gtg agg cct ctg cgg | 508 |
| Ala Pro Pro Gln Ile Arg Arg Pro Asn Arg Glu Val Arg Pro Leu Arg | |
|     110                115                120                   | |
| aaa gac gtg ggg gca gga gcc cgg gga ctc gtg ggc cga gca cac cag | 556 |
| Lys Asp Val Gly Ala Gly Ala Arg Gly Leu Val Gly Arg Ala His Gln | |
| 125                130                135                140    | |
| ata tcg aag agt gac aaa cct gca agt cgg gac aag gac tat aga gca | 604 |
| Ile Ser Lys Ser Asp Lys Pro Ala Ser Arg Asp Lys Asp Tyr Arg Ala | |
|             145                150                155           | |
| aga ggg aga gat gac aag gca agg aaa aat gtg caa gat ggt gca agt | 652 |
| Arg Gly Arg Asp Asp Lys Ala Arg Lys Asn Val Gln Asp Gly Ala Ser | |
|         160                165                170               | |
| gac agc gag att ccc aag ttt gat ggc gcc ggg tat gat aag gat ctg | 700 |
| Asp Ser Glu Ile Pro Lys Phe Asp Gly Ala Gly Tyr Asp Lys Asp Leu | |
|     175                180                185                   | |

```
gtg gaa gcc ctg gag agg gac att gtg tcc agg aac cct agc att cac    748
Val Glu Ala Leu Glu Arg Asp Ile Val Ser Arg Asn Pro Ser Ile His
    190             195             200 tgg gat gac ata gca gac ctg gag gag gct aag aag ttg ctc cgg gaa    796
Trp Asp Asp Ile Ala Asp Leu Glu Glu Ala Lys Lys Leu Leu Arg Glu
205             210             215             220 gct gtt gtc ctg ccc atg tgg atg cct gac ttt ttc aaa ggg att aga    844
Ala Val Val Leu Pro Met Trp Met Pro Asp Phe Phe Lys Gly Ile Arg
                225             230             235 agg cca tgg aag ggt gtg ctg atg gtt ggc ccc cca ggc act ggt aag    892
Arg Pro Trp Lys Gly Val Leu Met Val Gly Pro Pro Gly Thr Gly Lys
            240             245             250 act atg ctg gct aaa gcg gtt gcc act gaa tgt ggg aca acc ttt ttc    940
Thr Met Leu Ala Lys Ala Val Ala Thr Glu Cys Gly Thr Thr Phe Phe
        255             260             265 aac gtg tcc tct tct acc ctg aca tct aag tac aga ggc gaa tct gag    988
Asn Val Ser Ser Ser Thr Leu Thr Ser Lys Tyr Arg Gly Glu Ser Glu
    270             275             280 aag ttg gtc cga ctg ttg ttt gaa atg gct agg ttc tat gcc cct acc   1036
Lys Leu Val Arg Leu Leu Phe Glu Met Ala Arg Phe Tyr Ala Pro Thr
285             290             295             300 acg atc ttc atc gac gaa att gat tct atc tgc agt cga aga ggg acg   1084
Thr Ile Phe Ile Asp Glu Ile Asp Ser Ile Cys Ser Arg Arg Gly Thr
                305             310             315 tct gat gag cac gag gca agc cgc aga gtc aag tcg gag ctc ctc atc   1132
Ser Asp Glu His Glu Ala Ser Arg Arg Val Lys Ser Glu Leu Leu Ile
            320             325             330 cag atg gat gga gtt gga gga gcc tta gaa aat gat gac cca tcc aaa   1180
Gln Met Asp Gly Val Gly Gly Ala Leu Glu Asn Asp Asp Pro Ser Lys
        335             340             345 atg gtg atg gtc ctg gct gct acg aac ttt ccg tgg gac att gat gag   1228
Met Val Met Val Leu Ala Ala Thr Asn Phe Pro Trp Asp Ile Asp Glu
    350             355             360 gct ctg cgc agg aga cta gag aaa agg att tac att cct ctc ccg aca   1276
Ala Leu Arg Arg Arg Leu Glu Lys Arg Ile Tyr Ile Pro Leu Pro Thr
365             370             375             380 gca aaa gga aga gcg gag ctc ctg aag atc agc ctc cgg gag gta gag   1324
Ala Lys Gly Arg Ala Glu Leu Leu Lys Ile Ser Leu Arg Glu Val Glu
                385             390             395 ctg gac ccc gat gtc cac ctg gag gac atc gcc gac aag acg gag ggc   1372
Leu Asp Pro Asp Val His Leu Glu Asp Ile Ala Asp Lys Thr Glu Gly
            400             405             410 tac tcg ggt gcc gac atc act aac atc tgc agg gac gct tct ttg atg   1420
Tyr Ser Gly Ala Asp Ile Thr Asn Ile Cys Arg Asp Ala Ser Leu Met
        415             420             425 gcg atg agg cgg cgc atc aat ggc ttg agt ccg gaa gag atc cgg gcc   1468
Ala Met Arg Arg Arg Ile Asn Gly Leu Ser Pro Glu Glu Ile Arg Ala
    430             435             440 ctg tcc aag gag gag ctg cag atg cct gtc acc aga ggg gac ttg gag   1516
Leu Ser Lys Glu Glu Leu Gln Met Pro Val Thr Arg Gly Asp Leu Glu
445             450             455             460 ttg gct ctg aag aaa atc gcc aag tct gtc tca gcg gca gac ctg gag   1564
Leu Ala Leu Lys Lys Ile Ala Lys Ser Val Ser Ala Ala Asp Leu Glu
                465             470             475 aag tac gaa aag tgg atg gtt gag ttt ggg tct gca tga ttggtcagct    1613
Lys Tyr Glu Lys Trp Met Val Glu Phe Gly Ser Ala
            480             485 cttccatctc tgggagtttt ctttatgaaa tgtgaagaaa ttcctgaaat taaaaaaaaa  1673
```

-continued

```
aatctggaag ttttaatcag aggaatcttc acttgaaggc caaaccaaaa cagaaatgcc    1733
agaggtacag agaaatgtag ttgagaaaca aggtatgatc atacagtctg ctggctccag    1793
gctaccaaac ctcatacttg tgtacagaat aagagagcca gtggcccggg ctgaaggggt    1853
agctctgtgc agggagggcc ttgtttacaa agcattggca gagttttctt gcccatacgt    1913
gcactgactg gtagtttgga attgtcactt tgagtggaat gatcacaagt tcttcaggaa    1973 taattttaa atctctagaa tctaatactt cctgttagag ttgaaaatgt agttagtact     2033
cactcctctt agcttaccag ttcctctgtt agctgccgcc ttacatccac cagggaagag    2093
tctctgaccg actgctccgt tgacatttgc cctggcctgt agtctctgtg ccggggcctc    2153
tcctgcttcc tttgcaatga tgggaagagc ccttcttagt tagcagcagc cttcagcctt    2213
tgaagtcctc actcttcctt cagtactctc aagtcaatat ggctactgtt ttttctcacc    2273
tccaacactg tgtgcttttg tagaatttaa cctgtttagg tcggtaatct gagttccaaa    2333
caagactagt ctcctaggcg aatgcaaaag aacctttccc ctcttctgca tgtgagcgag    2393
cattctgcca gcacgcatgt ctgtatacca catgcatgca gtgcccgagg aggccagaga    2453
ggacattggg tcccctggtt ctggaattac agggtgtgtg agccaccgtg tggatgctgg    2513
gaaccaaacc caggtctcta aagggcagc cagtgttctt aacggctgag ccatccctcc     2573
aaccccacaa acagaaccta tgaacttgtg catgcagtgg gactagagca gacagctgcc    2633
atgctcgtta gatgcggagt aaccaggaag gaggatctca gacaggggcc gcatgagtgt    2693
ggtcacacgc actgtgccct gatgtccgtt ctctgtgatt aattacacct gcccttctgg    2753
atcaccaggc aacctatgct tcaaaagttt gtctaataat atcctgattc tcgagcctat    2813
tttaagctat atactatata caccttagag gcacttttaa aaactcctag tatgttgctt    2873
aagatatttg accccttttt cttactaaaa cctataaatg catcacgctc ttttcaggag    2933
acataagccc gactctctaa actcttggat tcatctgatt actgtaaatt tccccctttc    2993
ttctgagagg gagtgaaggg ccccagcagg ctgaccattg cacacacagc ggagcatagc    3053
agacatggca ctgacaggtt ttgtcgttta cccctctccc ccactgagct gttagcttga    3113
tcctgaagct cactaccaag gtctggcccc ttattcagtc actgactcat tcctgagacc    3173
gagcaccaag gtctagctat cagaattcag tatttcgact aacctaacta acataaccaa    3233
ccagatctta ccagcacgtt ctcgctcact ctaagacaga gctcccccctt tcctcttacg    3293 attaacacct gcaaagctat ttactgttgt ttctgtgtaa ttcagactca gccaccttgt    3353
ctcatctctc tgccttgctt aataaaggat ctctttgcat ttggcttgtg cttggacgga    3413 ggtgttgga tgtggtctgt gcctaacccg gggtccagag gggagcatcc cacagtgcac     3473
aggtcccttc gtaaggatta taaaatttca aatcaaaaga catttgtaat gggactaatt    3533
ttaaaattag actgagagac tcttccttcc atgaacaaac ttgcttttat ttatttactt    3593
tgaggaagag tctgactctg ttgccaatgc tggtcttcag ctgtttcagc ctcccagtag    3653
ctgggactga ttattgataa atgcttaaaa taaacaacta atgtggaagg ctgatgcagg    3713
aggatccata ggaaacagaa acagcccaaa tgccccccag ctgctgaaag tatgatgaaa    3773
atatcacaca cacacacaca cacacacaca cacacacaca cacgaagagt ctgaagccaa    3833
cttgtgtaga ctagcaaggc cctatctcaa aaatcaaaca gaaagaaccc cattcaatcc    3893
tcttgttgta tttcaaaaag aaggaaggaa ggaaggaagg aaggaaggaa ggaaggaagg    3953
aaggaaggaa ggaaggaaaa gaaaaagaa aagaaaagaa aagaaagaag aaagagaagg    4013
aaggaagacc gaccttctct ataaccctgc tggttggcag acctttcctg gctctggcat    4073
```

```
tagttacctt tgcataaacc catttttttt ctggagtcct catgcaccca cagtacaggc    4133
ctgcgtctac gctagggtag gtggtggtct gtagttagta agtcacatgt gcgctccctc    4193
catccctccc tcctcacaag ctgtcagtag acggcacaga tctgtaagag gccggccact    4253
cagatgtctc tctcctgtaa gacatgctgt ccacacattg tcactgccat ggcggcagga    4313
agcatgttac tctgcacaca gtaggaaaca ggagctctgg ggcagcagca caggggctgg    4373
tgtgtgcaca gttgtttcat cgtcccatca tgggcacacc gtgctggtca ccctcgctgt    4433
gtagatggtg ggtggaggct acgtgacttg ccaagtagtg ctggaccctg aagctgtggc    4493
tggacatttt ctccagtaac tgcctctcct ggctcctgct actaaagcac gagtttagtt    4553
tataactgga gagacagcga tctgtgtgtt tggagaagag aatatacaga aaggttttcc    4613
cctttgcttt tcttttgaaa cctttgattg gttttaaatt gtttaaaatg agttttaaac    4673
aattaaacag tttgcttaaa caatcaaaca attgtttgtt taaacacacc attaaaaatc    4733
aatcgatgaa agatctattt cagtgcaccc actttatcat ttttgtgcca cgattatacg    4793
tgtgattatg caaagcatac acgcaagtaa tgcgattact gtgaaagctt ccatagtttc    4853
ctttttaaag aaagtaagat aatattggtg agatgtccca gacaaatgga agctgtggcc    4913
tcctagttac gcaggttagg aacaggtgac atcacaggcc ttccacccat gagttccatc    4973
cttcagtaga gtgaccccag gcaacacatg gccatcagaa atgccagact gggacatcct    5033
gccggggcct tcacaggaga gcctgggtca cagttcagtc acacagctgt ctaactttca    5093
gggagttcac caagtggggt ggagtaggga aaccagcacc cacaagcagt caagcaggca    5153
cacggaggcc taaaacaagc agccgcccag gagtatgtgt gagcccagtt tacagtatta    5213
attgtcgctg gttatccctg tgtgtattgt gactctgtgg ggagtcattg cctccttagc    5273 tctttgggtat ctgagttcat gaggcttcct tccttagata cactacagga tcaggcagga   5333
gtctgcccag gtaacctcct ccttgcctca cttgagaggc aggcaaagaa ctgggcctgt    5393
catttgcata gtggtcttgg ctctggcctc cttagtgagg tcttttttgg tctcttcata    5453
cacacacaca cacacacgca cacaggcccc caataataat aatagtacat ttctactgtt    5513
ttcttattaa atatagatca caactagggt atgactcatg ctttgggata aaatgttagg    5573
tgggagtcga ccttttctaa gaaaagatct aactgtggcg aactggaaga atctggacta    5633
ttccagcttt ctagtgtctt tgttttgttg cttaatgttt gcatgtacaa tgttttaaat    5693
ttgtgacaca tatgatactt atgtcaatct aagagtccac cacaacagaa gaaaatagga    5753
ccaagttgaa ggatgcattg ggggcaaatt aaccctcacc gggaccgcac tgatattaaa    5813
gttgaaggat gggggcggg ggagggact aatcctcatg gggaccactc atccacaccg    5873
attatttctg cagtttattt acctcataat tattacatgt ttacttattt atgtgtttaa    5933
tttaggcttt ccttatttat ttaatttttg ggtcacttgc ttttgatatt atttcttaat    5993
gtggaaactg agtattaaaa atattagatc tgtatggtga tatgttttta cacatttact    6053
tagtagtaat ttgaattttt accagtttat ttttttttga aaaatgtagt tttgatgata    6113
attctcattt caggtgcctt attaataaaa gcttattaag aggaaaaaaa aaaaaaaaa     6173
```

<210> SEQ ID NO 6
<211> LENGTH: 488
<212> TYPE: PRT
<213> ORGANISM: Mus musculus

<400> SEQUENCE: 6

```
Met Asn Leu Ala Glu Ile Cys Glu Asn Ala Lys Lys Gly Arg Glu Tyr
1               5                   10                  15

Ala Leu Leu Gly Asn Tyr Asp Ser Ser Met Val Tyr Tyr Gln Gly Val
            20                  25                  30

Ile Gln Gln Ile Gln Arg His Cys Gln Ser Leu Arg Asp Pro Ala Thr
        35                  40                  45

Lys Ala Lys Trp Gln Gln Val Arg Gln Glu Leu Leu Glu Glu Tyr Glu
50                  55                  60

Gln Val Lys Ser Ile Val Ser Thr Leu Glu Ser Phe Lys Met Asp Lys
65                  70                  75                  80

Pro Pro Asp Phe Pro Val Ser Cys Arg Asp Glu Pro Phe Arg Asp Pro
            85                  90                  95

Ala Val Trp Pro Pro Val Pro Ala Glu His Arg Ala Pro Pro Gln
            100                 105                 110

Ile Arg Arg Pro Asn Arg Glu Val Arg Pro Leu Arg Lys Asp Val Gly
        115                 120                 125

Ala Gly Ala Arg Gly Leu Val Gly Arg Ala His Gln Ile Ser Lys Ser
        130                 135                 140

Asp Lys Pro Ala Ser Arg Asp Lys Asp Tyr Arg Ala Arg Gly Arg Asp
145                 150                 155                 160

Asp Lys Ala Arg Lys Asn Val Gln Asp Gly Ala Ser Asp Ser Glu Ile
            165                 170                 175

Pro Lys Phe Asp Gly Ala Gly Tyr Asp Lys Asp Leu Val Glu Ala Leu
            180                 185                 190

Glu Arg Asp Ile Val Ser Arg Asn Pro Ser Ile His Trp Asp Asp Ile
        195                 200                 205

Ala Asp Leu Glu Glu Ala Lys Lys Leu Leu Arg Glu Ala Val Val Leu
        210                 215                 220

Pro Met Trp Met Pro Asp Phe Phe Lys Gly Ile Arg Arg Pro Trp Lys
225                 230                 235                 240

Gly Val Leu Met Val Gly Pro Pro Gly Thr Gly Lys Thr Met Leu Ala
            245                 250                 255

Lys Ala Val Ala Thr Glu Cys Gly Thr Thr Phe Phe Asn Val Ser Ser
            260                 265                 270

Ser Thr Leu Thr Ser Lys Tyr Arg Gly Glu Ser Glu Lys Leu Val Arg
        275                 280                 285

Leu Leu Phe Glu Met Ala Arg Phe Tyr Ala Pro Thr Thr Ile Phe Ile
        290                 295                 300

Asp Glu Ile Asp Ser Ile Cys Ser Arg Arg Gly Thr Ser Asp Glu His
305                 310                 315                 320

Glu Ala Ser Arg Arg Val Lys Ser Glu Leu Leu Ile Gln Met Asp Gly
            325                 330                 335

Val Gly Gly Ala Leu Glu Asn Asp Asp Pro Ser Lys Met Val Met Val
            340                 345                 350

Leu Ala Ala Thr Asn Phe Pro Trp Asp Ile Asp Glu Ala Leu Arg Arg
            355                 360                 365

Arg Leu Glu Lys Arg Ile Tyr Ile Pro Leu Pro Thr Ala Lys Gly Arg
        370                 375                 380

Ala Glu Leu Leu Lys Ile Ser Leu Arg Glu Val Glu Leu Asp Pro Asp
385                 390                 395                 400

Val His Leu Glu Asp Ile Ala Asp Lys Thr Glu Gly Tyr Ser Gly Ala
            405                 410                 415

Asp Ile Thr Asn Ile Cys Arg Asp Ala Ser Leu Met Ala Met Arg Arg
```

```
                420                  425                  430
Arg Ile Asn Gly Leu Ser Pro Glu Glu Ile Arg Ala Leu Ser Lys Glu
            435                  440                  445

Glu Leu Gln Met Pro Val Thr Arg Gly Asp Leu Glu Leu Ala Leu Lys
        450                  455                  460

Lys Ile Ala Lys Ser Val Ser Ala Ala Asp Leu Glu Lys Tyr Glu Lys
465                  470                  475                  480

Trp Met Val Glu Phe Gly Ser Ala
                485

<210> SEQ ID NO 7
<211> LENGTH: 1559
<212> TYPE: DNA
<213> ORGANISM: Bos taurus
<220> FEATURE:
<221> NAME/KEY: CDS
<222> LOCATION: (1)..(1473)
<223> OTHER INFORMATION:

<400> SEQUENCE: 7 atg aat ttg gct gag att tgt gac aat gca aag aaa gga aga gaa tat        48
Met Asn Leu Ala Glu Ile Cys Asp Asn Ala Lys Lys Gly Arg Glu Tyr
1               5                   10                  15 gca ctt ctt gga aat tat gac tca tcc atg gta tat tac cag ggg gtg       96
Ala Leu Leu Gly Asn Tyr Asp Ser Ser Met Val Tyr Tyr Gln Gly Val
            20                  25                  30 atc cag cag att cag aga cat tgc cag tca gtc aga gac cca gcg gtc      144
Ile Gln Gln Ile Gln Arg His Cys Gln Ser Val Arg Asp Pro Ala Val
        35                  40                  45 aaa ggc aga tgg cag cag gtt cgg cag gaa tta ttg gaa gaa tat gaa      192
Lys Gly Arg Trp Gln Gln Val Arg Gln Glu Leu Leu Glu Glu Tyr Glu
    50                  55                  60 caa gtt aaa agt att gtc agt act ttg gaa agt ttt aaa atc gac agg      240
Gln Val Lys Ser Ile Val Ser Thr Leu Glu Ser Phe Lys Ile Asp Arg
65                  70                  75                  80 ccc cca gat ttc cct gtg tcc tgt caa gat gaa ccg ttt aga gat cct      288
Pro Pro Asp Phe Pro Val Ser Cys Gln Asp Glu Pro Phe Arg Asp Pro
                85                  90                  95 gcc gtg tgg ccg ccc ccc gta cct gca gaa cac aaa gct cca cct cag      336
Ala Val Trp Pro Pro Pro Val Pro Ala Glu His Lys Ala Pro Pro Gln
            100                 105                 110 ata agg cgt ccc aat cga gaa gta aga cct ctg agg aaa gag atg cca      384
Ile Arg Arg Pro Asn Arg Glu Val Arg Pro Leu Arg Lys Glu Met Pro
        115                 120                 125 gga ggc ggc gcc cgg gga cct gta ggc cga gca cat ccc ata tct aag      432
Gly Gly Gly Ala Arg Gly Pro Val Gly Arg Ala His Pro Ile Ser Lys
    130                 135                 140 agc gag aag ccc tcc acc agc agg gac aag gac tgc aga gcc aga ggg      480
Ser Glu Lys Pro Ser Thr Ser Arg Asp Lys Asp Cys Arg Ala Arg Gly
145                 150                 155                 160 aga gat gac aag gga agg aaa aat atg caa gat ggt aca agt gat ggt      528
Arg Asp Asp Lys Gly Arg Lys Asn Met Gln Asp Gly Thr Ser Asp Gly
                165                 170                 175 gaa att cca aaa ttt gat ggt gct gca tat gat aag gac ctg gtg gaa      576
Glu Ile Pro Lys Phe Asp Gly Ala Ala Tyr Asp Lys Asp Leu Val Glu
            180                 185                 190 gcc ctt gag aga gac atc gtc tcc agg aac cca agt gtt cac tgg gat      624
Ala Leu Glu Arg Asp Ile Val Ser Arg Asn Pro Ser Val His Trp Asp
        195                 200                 205 gac ata gca gat ctg gaa gaa gct aag aag ttg ctg aga gaa gct gtc      672
```

```
                Asp Ile Ala Asp Leu Glu Glu Ala Lys Lys Leu Leu Arg Glu Ala Val
                    210                 215                 220 gtc ctt ccc atg tgg atg cct gac ttt ttc aaa ggg att aga agg cca            720
Val Leu Pro Met Trp Met Pro Asp Phe Phe Lys Gly Ile Arg Arg Pro
225                 230                 235                 240 tgg aag gga gtg ctg atg gtt ggg ccc cca ggc act gga aag acc atg            768
Trp Lys Gly Val Leu Met Val Gly Pro Pro Gly Thr Gly Lys Thr Met
                245                 250                 255 ctg gct aaa gcc gtg gcc acc gag tgc ggc aca acc ttc ttt aat gtc            816
Leu Ala Lys Ala Val Ala Thr Glu Cys Gly Thr Thr Phe Phe Asn Val
            260                 265                 270 tcc tct tcc aca ctg acg tct aaa tat aga ggc gaa tct gag aag ttg            864
Ser Ser Ser Thr Leu Thr Ser Lys Tyr Arg Gly Glu Ser Glu Lys Leu
        275                 280                 285 gtt cgt ctg ttg ttt gaa atg gct agg ttt tat gcc ccc acc acg atc            912
Val Arg Leu Leu Phe Glu Met Ala Arg Phe Tyr Ala Pro Thr Thr Ile
    290                 295                 300 ttc atc gat gag ata gat tct atc tgc agt cga aga gga acc tct gat            960
Phe Ile Asp Glu Ile Asp Ser Ile Cys Ser Arg Arg Gly Thr Ser Asp
305                 310                 315                 320 gaa cat gag gca agt cgc aga gtc aag tct gag ctg ctc att cag atg            1008
Glu His Glu Ala Ser Arg Arg Val Lys Ser Glu Leu Leu Ile Gln Met
                325                 330                 335 gat gga gta gga gga gct ttg gag aat gat gat cct tcc aaa atg gtc            1056
Asp Gly Val Gly Gly Ala Leu Glu Asn Asp Asp Pro Ser Lys Met Val
                340                 345                 350 atg gta ttg gct gcc act aac ttc cca tgg gac att gat gaa gca ttg            1104
Met Val Leu Ala Ala Thr Asn Phe Pro Trp Asp Ile Asp Glu Ala Leu
            355                 360                 365 cgg agg aga tta gaa aaa agg ata tat ata cct ctg ccg aca gca aaa            1152
Arg Arg Arg Leu Glu Lys Arg Ile Tyr Ile Pro Leu Pro Thr Ala Lys
        370                 375                 380 gga aga act gag ctt ctg aaa atc aat ctt cgt gag gtt gag ctg gat            1200
Gly Arg Thr Glu Leu Leu Lys Ile Asn Leu Arg Glu Val Glu Leu Asp
385                 390                 395                 400 cca gat att caa ctg gaa gat ata gca gag aag att gag ggg tac tct            1248
Pro Asp Ile Gln Leu Glu Asp Ile Ala Glu Lys Ile Glu Gly Tyr Ser
                405                 410                 415 ggt gct gat ata act aac gtt tgc agg gat gca tcc tta atg gcc atg            1296
Gly Ala Asp Ile Thr Asn Val Cys Arg Asp Ala Ser Leu Met Ala Met
                420                 425                 430 aga cgg cga atc aac ggt ctc agt cca gaa gag atc cgt gca ctc tct            1344
Arg Arg Arg Ile Asn Gly Leu Ser Pro Glu Glu Ile Arg Ala Leu Ser
            435                 440                 445 aaa gag gag ctt cag atg ccc gtg acc aga gga gac ttt gag ttg gct            1392
Lys Glu Glu Leu Gln Met Pro Val Thr Arg Gly Asp Phe Glu Leu Ala
450                 455                 460 ctt aag aaa atc gca aag tct gtc tct gca gca gac tta gag aaa tat            1440
Leu Lys Lys Ile Ala Lys Ser Val Ser Ala Ala Asp Leu Glu Lys Tyr
465                 470                 475                 480 gaa aag tgg atg gta gaa ttt gga tct gct tga atttctgtca gctctttcat          1493
Glu Lys Trp Met Val Glu Phe Gly Ser Ala
                485                 490 ttctggtatt tttgtctata aaatgtgaag aaattccagc aatttttttt tttaaaacag          1553
gtttga                                                                     1559

<210> SEQ ID NO 8
<211> LENGTH: 490
<212> TYPE: PRT
```

<213> ORGANISM: Bos taurus

<400> SEQUENCE: 8

| | | | | | | | | | | | |
|---|---|---|---|---|---|---|---|---|---|---|---|
|Met|Asn|Leu|Ala|Glu|Ile|Cys|Asp|Asn|Ala|Lys|Lys|Gly|Arg|Glu|Tyr|
|1| | | |5| | | |10| | | | | |15| |

Ala Leu Leu Gly Asn Tyr Asp Ser Ser Met Val Tyr Tyr Gln Gly Val
          20                  25                  30

Ile Gln Gln Ile Gln Arg His Cys Gln Ser Val Arg Asp Pro Ala Val
              35                  40                  45

Lys Gly Arg Trp Gln Gln Val Arg Gln Glu Leu Leu Glu Glu Tyr Glu
 50                  55                  60

Gln Val Lys Ser Ile Val Ser Thr Leu Glu Ser Phe Lys Ile Asp Arg
65                  70                  75                  80

Pro Pro Asp Phe Pro Val Ser Cys Gln Asp Glu Pro Phe Arg Asp Pro
                 85                  90                  95

Ala Val Trp Pro Pro Val Pro Ala Glu His Lys Ala Pro Pro Gln
                100                 105                 110

Ile Arg Arg Pro Asn Arg Glu Val Arg Pro Leu Arg Lys Glu Met Pro
            115                 120                 125

Gly Gly Gly Ala Arg Gly Pro Val Gly Arg Ala His Pro Ile Ser Lys
130                 135                 140

Ser Glu Lys Pro Ser Thr Ser Arg Asp Lys Asp Cys Arg Ala Arg Gly
145                 150                 155                 160

Arg Asp Asp Lys Gly Arg Lys Asn Met Gln Asp Gly Thr Ser Asp Gly
                165                 170                 175

Glu Ile Pro Lys Phe Asp Gly Ala Ala Tyr Asp Lys Asp Leu Val Glu
            180                 185                 190

Ala Leu Glu Arg Asp Ile Val Ser Arg Asn Pro Ser Val His Trp Asp
        195                 200                 205

Asp Ile Ala Asp Leu Glu Glu Ala Lys Lys Leu Leu Arg Glu Ala Val
    210                 215                 220

Val Leu Pro Met Trp Met Pro Asp Phe Phe Lys Gly Ile Arg Arg Pro
225                 230                 235                 240

Trp Lys Gly Val Leu Met Val Gly Pro Pro Gly Thr Gly Lys Thr Met
                245                 250                 255

Leu Ala Lys Ala Val Ala Thr Glu Cys Gly Thr Thr Phe Phe Asn Val
            260                 265                 270

Ser Ser Ser Thr Leu Thr Ser Lys Tyr Arg Gly Glu Ser Glu Lys Leu
        275                 280                 285

Val Arg Leu Leu Phe Glu Met Ala Arg Phe Tyr Ala Pro Thr Thr Ile
    290                 295                 300

Phe Ile Asp Glu Ile Asp Ser Ile Cys Ser Arg Arg Gly Thr Ser Asp
305                 310                 315                 320

Glu His Glu Ala Ser Arg Arg Val Lys Ser Glu Leu Leu Ile Gln Met
                325                 330                 335

Asp Gly Val Gly Gly Ala Leu Glu Asn Asp Asp Pro Ser Lys Met Val
            340                 345                 350

Met Val Leu Ala Ala Thr Asn Phe Pro Trp Asp Ile Asp Glu Ala Leu
        355                 360                 365

Arg Arg Arg Leu Glu Lys Arg Ile Tyr Ile Pro Leu Pro Thr Ala Lys
    370                 375                 380

Gly Arg Thr Glu Leu Leu Lys Ile Asn Leu Arg Glu Val Glu Leu Asp
385                 390                 395                 400

-continued

```
Pro Asp Ile Gln Leu Glu Asp Ile Ala Glu Lys Ile Glu Gly Tyr Ser
                405                 410                 415

Gly Ala Asp Ile Thr Asn Val Cys Arg Asp Ala Ser Leu Met Ala Met
            420                 425                 430

Arg Arg Arg Ile Asn Gly Leu Ser Pro Glu Glu Ile Arg Ala Leu Ser
        435                 440                 445

Lys Glu Glu Leu Gln Met Pro Val Thr Arg Gly Asp Phe Glu Leu Ala
    450                 455                 460

Leu Lys Lys Ile Ala Lys Ser Val Ser Ala Ala Asp Leu Glu Lys Tyr
465                 470                 475                 480

Glu Lys Trp Met Val Glu Phe Gly Ser Ala
                485                 490
```

<210> SEQ ID NO 9
<211> LENGTH: 2274
<212> TYPE: DNA
<213> ORGANISM: Equus caballus
<220> FEATURE:
<221> NAME/KEY: CDS
<222> LOCATION: (1)..(2013)
<223> OTHER INFORMATION:

<400> SEQUENCE: 9

```
atg ggc gcg gag gag ggc tgg acc aga cgc tct tca ccg agc cgg gcg       48
Met Gly Ala Glu Glu Gly Trp Thr Arg Arg Ser Ser Pro Ser Arg Ala
1               5                   10                  15 cgg aga cgc cct gct gtt cct tcc tct gac cag cat ctc gag aca gcg       96
Arg Arg Arg Pro Ala Val Pro Ser Ser Asp Gln His Leu Glu Thr Ala
                20                  25                  30 cag cgc ggg cag cag cgc gct ccg cga gac aga cac gcg tcc tgc cac      144
Gln Arg Gly Gln Gln Arg Ala Pro Arg Asp Arg His Ala Ser Cys His
            35                  40                  45 ggg gac gag gcg ctg ccg cgg cag gca gaa cca gcg ctc aat cat tac      192
Gly Asp Glu Ala Leu Pro Arg Gln Ala Glu Pro Ala Leu Asn His Tyr
        50                  55                  60 acc ctg tcc ccg gcc gcg gga gac agg cgg cgt ttt cac aaa gag att      240
Thr Leu Ser Pro Ala Ala Gly Asp Arg Arg Arg Phe His Lys Glu Ile
65                  70                  75                  80 ctc cgg cgc ggg ccg cgg tgc ggg agg ggg aga gca gag gac gcg cga      288
Leu Arg Arg Gly Pro Arg Cys Gly Arg Gly Arg Ala Glu Asp Ala Arg
                85                  90                  95 gcc tcg gcg ggc att atg ggg att gta gtt cag cgg ctc cct cgg cct      336
Ala Ser Ala Gly Ile Met Gly Ile Val Val Gln Arg Leu Pro Arg Pro
                100                 105                 110 cgc gcc ctt ggc ggg gtg cct gga cgg gcg aac tac aaa gcc cgg cgc      384
Arg Ala Leu Gly Gly Val Pro Gly Arg Ala Asn Tyr Lys Ala Arg Arg
            115                 120                 125 ccc gac agc tgg gaa aga ccg ata act ttg agc cga cca gga gaa gag      432
Pro Asp Ser Trp Glu Arg Pro Ile Thr Leu Ser Arg Pro Gly Glu Glu
        130                 135                 140 aaa tct ctc ttt gtg gtg agg ggc ctc atg ggt ggt cgc gat ttg ggc      480
Lys Ser Leu Phe Val Val Arg Gly Leu Met Gly Gly Arg Asp Leu Gly
145                 150                 155                 160 tct gtg cgc tgg gaa ggg gaa gtg gag ttg aga cgt gtg ctt ccc gcc      528
Ser Val Arg Trp Glu Gly Glu Val Glu Leu Arg Arg Val Leu Pro Ala
                165                 170                 175 ctg cca ttt ggc cgg ccg ggc tac agc gct cag ccc cac ccc ggc tgg      576
Leu Pro Phe Gly Arg Pro Gly Tyr Ser Ala Gln Pro His Pro Gly Trp
                180                 185                 190 gcc gcc gcc cgc cta gtc tca ggg atg agc agc cgc cca ggc tgc agg      624
```

|     |     |     |     |     |     |     |     |     |     |     |     |     |     |     |
| --- | --- | --- | --- | --- | --- | --- | --- | --- | --- | --- | --- | --- | --- | --- |
| Ala | Ala | Ala 195 | Arg | Leu | Val | Ser 200 | Gly | Met | Ser | Ser 205 | Arg | Pro | Gly | Cys | Arg |

| | | | | | | | | | | | | | |
| --- | --- | --- | --- | --- | --- | --- | --- | --- | --- | --- | --- | --- | --- |
| gcc | tcg | ggc | ctt | cgg | cgc | ctc | tca | ccc | tcc | cag | gtt | gct | gcc | gct | cgg | 672 |
| Ala | Ser 210 | Gly | Leu | Arg | Arg 215 | Leu | Ser | Pro | Ser | Gln 220 | Val | Ala | Ala | Arg |

| tgc | aga | acc | cat | aaa | ggt | tat | ttt | ttt | aag | gtt | cgg | cag | gaa | tta | ttg | 720 |
| Cys 225 | Arg | Thr | His | Lys 230 | Gly | Tyr | Phe | Phe | Lys 235 | Val | Arg | Gln | Glu | Leu 240 | Leu |

| gaa | gaa | tat | gaa | caa | gtt | aaa | agt | att | gtc | agc | act | ttg | gag | agt | ttt | 768 |
| Glu | Glu | Tyr | Glu | Gln 245 | Val | Lys | Ser | Ile | Val 250 | Ser | Thr | Leu | Glu | Ser 255 | Phe |

| aaa | att | gac | aag | ccc | cca | gat | ttc | cct | gtg | tct | tct | caa | gat | gaa | ccg | 816 |
| Lys | Ile | Asp | Lys 260 | Pro | Pro | Asp | Phe | Pro 265 | Val | Ser | Ser | Gln | Asp 270 | Glu | Pro |

| ttt | aga | gat | ccc | gct | gtt | tgg | ccg | ccc | cct | gta | cct | gca | gaa | cac | aga | 864 |
| Phe | Arg | Asp | Pro 275 | Ala | Val | Trp | Pro | Pro 280 | Pro | Val | Pro | Ala | Glu 285 | His | Arg |

| gct | ccg | cct | cag | ata | agg | cgc | ccc | aat | cga | gaa | gta | aga | cct | ctg | aga | 912 |
| Ala | Pro | Pro | Gln 290 | Ile | Arg | Arg | Pro | Asn 295 | Arg | Glu | Val | Arg | Pro 300 | Leu | Arg |

| aaa | gaa | atg | cca | gga | gta | gga | gcc | cgg | gga | cct | gtc | ggc | cga | gcg | cat | 960 |
| Lys | Glu | Met | Pro | Gly 310 | Val | Gly | Ala | Arg | Gly 315 | Pro | Val | Gly | Arg | Ala 320 | His |
| 305 | | | | | | | | | | | | | | | |

| cct | ata | tca | aag | agt | gaa | aaa | ccc | tcc | aca | agt | agg | gac | aag | gat | tac | 1008 |
| Pro | Ile | Ser | Lys | Ser 325 | Glu | Lys | Pro | Ser | Thr 330 | Ser | Arg | Asp | Lys | Asp 335 | Tyr |

| aga | gcc | aaa | ggg | aga | gat | gac | aag | gga | agg | aaa | cat | atg | caa | gat | ggt | 1056 |
| Arg | Ala | Lys | Gly 340 | Arg | Asp | Asp | Lys | Gly 345 | Arg | Lys | His | Met | Gln 350 | Asp | Gly |

| gca | agt | gat | ggt | gaa | att | cca | aaa | ttt | gat | ggt | gct | gga | tat | gat | aag | 1104 |
| Ala | Ser | Asp | Gly 355 | Glu | Ile | Pro | Lys | Phe 360 | Asp | Gly | Ala | Gly | Tyr 365 | Asp | Lys |

| gac | ttg | gtg | gag | gcc | ctc | gag | aga | gac | atc | gtg | tcc | agg | aat | cct | agc | 1152 |
| Asp | Leu | Val | Glu 370 | Ala | Leu | Glu | Arg | Asp 375 | Ile | Val | Ser | Arg | Asn 380 | Pro | Ser |

| att | cat | tgg | gat | gac | ata | gcg | gat | ctg | gaa | gaa | gct | aag | aag | ttg | ctg | 1200 |
| Ile | His | Trp | Asp | Asp 390 | Ile | Ala | Asp | Leu | Glu 395 | Glu | Ala | Lys | Lys | Leu 400 | Leu |
| 385 | | | | | | | | | | | | | | | |

| agg | gaa | gct | gtt | gtt | ctt | ccg | atg | tgg | atg | cct | gac | ttc | ttc | aaa | ggg | 1248 |
| Arg | Glu | Ala | Val | Val 405 | Leu | Pro | Met | Trp | Met 410 | Pro | Asp | Phe | Phe | Lys 415 | Gly |

| att | aga | agg | cca | tgg | aag | ggt | gtg | ctg | atg | gtt | gga | ccc | cca | ggc | act | 1296 |
| Ile | Arg | Arg | Pro | Trp 420 | Lys | Gly | Val | Leu | Met 425 | Val | Gly | Pro | Pro | Gly 430 | Thr |

| ggt | aag | act | atg | cta | gct | aaa | gct | gtc | gcc | acg | gaa | tgt | ggc | aca | acg | 1344 |
| Gly | Lys | Thr | Met | Leu 435 | Ala | Lys | Ala | Val | Ala 440 | Thr | Glu | Cys | Gly | Thr 445 | Thr |

| ttc | ttc | aac | gtt | tcc | tct | tct | aca | ctg | acg | tct | aaa | tat | aga | ggt | gaa | 1392 |
| Phe | Phe | Asn | Val | Ser 450 | Ser | Ser | Thr | Leu | Thr 455 | Ser | Lys | Tyr | Arg | Gly 460 | Glu |

| tct | gag | aag | tta | gtc | cgt | ctg | ttg | ttt | gaa | atg | gct | aga | ttt | tat | gcc | 1440 |
| Ser | Glu | Lys | Leu | Val 470 | Arg | Leu | Leu | Phe | Glu 475 | Met | Ala | Arg | Phe | Tyr 480 | Ala |
| 465 | | | | | | | | | | | | | | | |

| ccc | acc | aca | atc | ttc | att | gat | gag | ata | gat | tct | atc | tgc | agt | cga | aga | 1488 |
| Pro | Thr | Thr | Ile | Phe 485 | Ile | Asp | Glu | Ile | Asp 490 | Ser | Ile | Cys | Ser | Arg 495 | Arg |

| gga | acc | tct | gat | gaa | cat | gag | gcc | agt | cgc | aga | gtc | aag | tct | gaa | cta | 1536 |
| Gly | Thr | Ser | Asp | Glu 500 | His | Glu | Ala | Ser | Arg 505 | Arg | Val | Lys | Ser | Glu 510 | Leu |

```
ctc att cag atg gat gga gtt gga gga gct tta gag aat gac gat cct   1584
Leu Ile Gln Met Asp Gly Val Gly Gly Ala Leu Glu Asn Asp Asp Pro
        515                 520                 525 tcc aaa atg gtt atg gtg ttg gct gct act aat ttc cca tgg gac att   1632
Ser Lys Met Val Met Val Leu Ala Ala Thr Asn Phe Pro Trp Asp Ile
    530                 535                 540 gat gaa gct ttg cga agg aga tta gaa aaa agg ata tat ata cca ctc   1680
Asp Glu Ala Leu Arg Arg Arg Leu Glu Lys Arg Ile Tyr Ile Pro Leu
545                 550                 555                 560 cca aca gca aaa gga aga act gag ctt ctg aag atc aat ctt cgt gag   1728
Pro Thr Ala Lys Gly Arg Thr Glu Leu Leu Lys Ile Asn Leu Arg Glu
                565                 570                 575 gtt gaa gtg gac cct gat att caa ctg gaa gat ata gca gag aag att   1776
Val Glu Val Asp Pro Asp Ile Gln Leu Glu Asp Ile Ala Glu Lys Ile
            580                 585                 590 gag ggc tat tct ggt gct gat ata act aat gtt tgc agg gat gcc tct   1824
Glu Gly Tyr Ser Gly Ala Asp Ile Thr Asn Val Cys Arg Asp Ala Ser
        595                 600                 605 tta atg gca atg aga cgg cga atc aat ggc tta agt cca gaa gag atc   1872
Leu Met Ala Met Arg Arg Arg Ile Asn Gly Leu Ser Pro Glu Glu Ile
    610                 615                 620 cgt gcg ctt tct aaa gag gag ctt cag atg cct gtg acc aga gga gac   1920
Arg Ala Leu Ser Lys Glu Glu Leu Gln Met Pro Val Thr Arg Gly Asp
625                 630                 635                 640 ttc gaa ttg gct ctt aag aaa att gct aag tct gtc tct gcc gca gac   1968
Phe Glu Leu Ala Leu Lys Lys Ile Ala Lys Ser Val Ser Ala Ala Asp
                645                 650                 655 ttg gag aag tat gaa aaa tgg atg gtt gaa ttt gga tct gct tga        2013
Leu Glu Lys Tyr Glu Lys Trp Met Val Glu Phe Gly Ser Ala
            660                 665                 670 atttctgaca ggtctttcat ttctggtatt tttgtttata aaatgtgaag aattcctgca   2073
attaaaaaaa aaaaataggt ttggaacttt tcgttggaga gattttcacg taaaggaaaa   2133
aaaaaacccc taaaaccaca aagaatataa atgtagttga gaaataagaa aagcttacgt   2193
agagagcctg atagtctccg tccctggct tgtgctggt attccacgtg ctcatgcatt    2253
ggtattgcac gcccagacca g                                            2274
```

<210> SEQ ID NO 10
<211> LENGTH: 670
<212> TYPE: PRT
<213> ORGANISM: Equus caballus

<400> SEQUENCE: 10

```
Met Gly Ala Glu Glu Gly Trp Thr Arg Arg Ser Ser Pro Ser Arg Ala
1               5                   10                  15

Arg Arg Arg Pro Ala Val Pro Ser Ser Asp Gln His Leu Glu Thr Ala
            20                  25                  30

Gln Arg Gly Gln Gln Arg Ala Pro Arg Asp Arg His Ala Ser Cys His
        35                  40                  45

Gly Asp Glu Ala Leu Pro Arg Gln Ala Glu Pro Ala Leu Asn His Tyr
    50                  55                  60

Thr Leu Ser Pro Ala Ala Gly Asp Arg Arg Arg Phe His Lys Glu Ile
65                  70                  75                  80

Leu Arg Arg Gly Pro Arg Cys Gly Arg Gly Arg Ala Glu Asp Ala Arg
                85                  90                  95

Ala Ser Ala Gly Ile Met Gly Ile Val Val Gln Arg Leu Pro Arg Pro
            100                 105                 110
```

```
Arg Ala Leu Gly Gly Val Pro Gly Arg Ala Asn Tyr Lys Ala Arg Arg
            115                 120                 125

Pro Asp Ser Trp Glu Arg Pro Ile Thr Leu Ser Arg Pro Gly Glu Glu
130                 135                 140

Lys Ser Leu Phe Val Val Arg Gly Leu Met Gly Gly Arg Asp Leu Gly
145                 150                 155                 160

Ser Val Arg Trp Glu Gly Val Glu Leu Arg Arg Val Leu Pro Ala
                165                 170                 175

Leu Pro Phe Gly Arg Pro Gly Tyr Ser Ala Gln Pro His Pro Gly Trp
            180                 185                 190

Ala Ala Ala Arg Leu Val Ser Gly Met Ser Ser Arg Pro Gly Cys Arg
            195                 200                 205

Ala Ser Gly Leu Arg Arg Leu Ser Pro Ser Gln Val Ala Ala Arg
210                 215                 220

Cys Arg Thr His Lys Gly Tyr Phe Phe Lys Val Arg Gln Glu Leu Leu
225                 230                 235                 240

Glu Glu Tyr Glu Gln Val Lys Ser Ile Val Ser Thr Leu Glu Ser Phe
                245                 250                 255

Lys Ile Asp Lys Pro Asp Phe Pro Val Ser Ser Gln Asp Glu Pro
            260                 265                 270

Phe Arg Asp Pro Ala Val Trp Pro Pro Val Pro Ala Glu His Arg
275                 280                 285

Ala Pro Pro Gln Ile Arg Arg Pro Asn Arg Glu Val Arg Pro Leu Arg
290                 295                 300

Lys Glu Met Pro Gly Val Gly Ala Arg Gly Pro Val Gly Arg Ala His
305                 310                 315                 320

Pro Ile Ser Lys Ser Glu Lys Pro Ser Thr Ser Arg Asp Lys Asp Tyr
                325                 330                 335

Arg Ala Lys Gly Arg Asp Asp Lys Gly Arg Lys His Met Gln Asp Gly
            340                 345                 350

Ala Ser Asp Gly Glu Ile Pro Lys Phe Asp Gly Ala Gly Tyr Asp Lys
            355                 360                 365

Asp Leu Val Glu Ala Leu Glu Arg Asp Ile Val Ser Arg Asn Pro Ser
370                 375                 380

Ile His Trp Asp Asp Ile Ala Asp Leu Glu Glu Ala Lys Lys Leu Leu
385                 390                 395                 400

Arg Glu Ala Val Val Leu Pro Met Trp Met Pro Asp Phe Phe Lys Gly
                405                 410                 415

Ile Arg Arg Pro Trp Lys Gly Val Leu Met Val Gly Pro Pro Gly Thr
            420                 425                 430

Gly Lys Thr Met Leu Ala Lys Ala Val Ala Thr Glu Cys Gly Thr Thr
            435                 440                 445

Phe Phe Asn Val Ser Ser Ser Thr Leu Thr Ser Lys Tyr Arg Gly Glu
450                 455                 460

Ser Glu Lys Leu Val Arg Leu Leu Phe Glu Met Ala Arg Phe Tyr Ala
465                 470                 475                 480

Pro Thr Thr Ile Phe Ile Asp Glu Ile Asp Ser Ile Cys Ser Arg Arg
                485                 490                 495

Gly Thr Ser Asp Glu His Glu Ala Ser Arg Arg Val Lys Ser Glu Leu
            500                 505                 510

Leu Ile Gln Met Asp Gly Val Gly Gly Ala Leu Glu Asn Asp Pro
            515                 520                 525

Ser Lys Met Val Met Val Leu Ala Ala Thr Asn Phe Pro Trp Asp Ile
```

```
                  530                 535                 540
Asp Glu Ala Leu Arg Arg Arg Leu Glu Lys Arg Ile Tyr Ile Pro Leu
545                 550                 555                 560

Pro Thr Ala Lys Gly Arg Thr Glu Leu Leu Lys Ile Asn Leu Arg Glu
                565                 570                 575

Val Glu Val Asp Pro Asp Ile Gln Leu Glu Asp Ile Ala Glu Lys Ile
                    580                 585                 590

Glu Gly Tyr Ser Gly Ala Asp Ile Thr Asn Val Cys Arg Asp Ala Ser
                595                 600                 605

Leu Met Ala Met Arg Arg Arg Ile Asn Gly Leu Ser Pro Glu Glu Ile
                610                 615                 620

Arg Ala Leu Ser Lys Glu Glu Leu Gln Met Pro Val Thr Arg Gly Asp
625                 630                 635                 640

Phe Glu Leu Ala Leu Lys Lys Ile Ala Lys Ser Val Ser Ala Ala Asp
                    645                 650                 655

Leu Glu Lys Tyr Glu Lys Trp Met Val Glu Phe Gly Ser Ala
                660                 665                 670

<210> SEQ ID NO 11
<211> LENGTH: 1784
<212> TYPE: DNA
<213> ORGANISM: Gallus gallus
<220> FEATURE:
<221> NAME/KEY: CDS
<222> LOCATION: (106)..(1575)
<223> OTHER INFORMATION:

<400> SEQUENCE: 11 cgccccctt  cctcgctctg  cttgagcgca  gaaggaccgc  gtcccctcc   ccgctccgcc         60 ggcgccggga  cacgcacccc  gctcctccca  ggtttctgag  agaag atg aat ttg gca        117
                                                      Met Asn Leu Ala
                                                       1 gag atc tgc gac aat gcc aaa aag gga aga gac tat gca ctc att ggg             165
Glu Ile Cys Asp Asn Ala Lys Lys Gly Arg Asp Tyr Ala Leu Ile Gly
 5                  10                  15                  20 aat tat gac tct tct atg gtg tat tac cag ggt gtc atc cag caa atc             213
Asn Tyr Asp Ser Ser Met Val Tyr Tyr Gln Gly Val Ile Gln Gln Ile
                 25                  30                  35 cag aga cat tgc cag tcg atc aga gat cca gca att aag ggc aaa tgg             261
Gln Arg His Cys Gln Ser Ile Arg Asp Pro Ala Ile Lys Gly Lys Trp
             40                  45                  50 caa cag gtt cgg caa gaa tta gtc gaa gaa tat gag caa gtt aag agc             309
Gln Gln Val Arg Gln Glu Leu Val Glu Glu Tyr Glu Gln Val Lys Ser
         55                  60                  65 att gtc gac act tta gag agt ttt aaa atg gac aga cct gca gat atc             357
Ile Val Asp Thr Leu Glu Ser Phe Lys Met Asp Arg Pro Ala Asp Ile
 70                  75                  80 cct gtg tcc tat caa gat gag cct ttt aga gac cct gct gtt tgg cca             405
Pro Val Ser Tyr Gln Asp Glu Pro Phe Arg Asp Pro Ala Val Trp Pro
 85                  90                  95                 100 cct cca gtt cca gct gaa cac agg gcc cca cct cag ata aag cgt ccc             453
Pro Pro Val Pro Ala Glu His Arg Ala Pro Pro Gln Ile Lys Arg Pro
                    105                 110                 115 aac cga gga gca aag ccc ttg agg aag gaa tcc ccg ggc ctg cag ccc             501
Asn Arg Gly Ala Lys Pro Leu Arg Lys Glu Ser Pro Gly Leu Gln Pro
                120                 125                 130 cgt ggg ccc gtg ggc aga gca cag cca gca gtg agg agc gac aaa cct             549
Arg Gly Pro Val Gly Arg Ala Gln Pro Ala Val Arg Ser Asp Lys Pro
            135                 140                 145
```

```
gca ggc agc cgt gac agg gag ccg agg gcc aga ggg agg gat gac aag    597
Ala Gly Ser Arg Asp Arg Glu Pro Arg Ala Arg Gly Arg Asp Asp Lys
    150                 155                 160 gga aag aaa ata ccc cag gaa ggt gtt gct gat gat gtt cta aga ttt    645
Gly Lys Lys Ile Pro Gln Glu Gly Val Ala Asp Asp Val Leu Arg Phe
165                 170                 175                 180 gat gga gcg ggt tat gac aaa gac ttg gtc gaa gct ctt gaa agg gac    693
Asp Gly Ala Gly Tyr Asp Lys Asp Leu Val Glu Ala Leu Glu Arg Asp
                185                 190                 195 att gtg tca agg aat cca agc att cac tgg gat gac ata gca gat ttg    741
Ile Val Ser Arg Asn Pro Ser Ile His Trp Asp Asp Ile Ala Asp Leu
            200                 205                 210 gaa gaa gcc aag aaa tta tta aga gaa gct gtt gtt ctt cca atg tgg    789
Glu Glu Ala Lys Lys Leu Leu Arg Glu Ala Val Val Leu Pro Met Trp
        215                 220                 225 atg cct gat ttt ttc aaa ggg atc aga agg cct tgg aag ggc gtg ctg    837
Met Pro Asp Phe Phe Lys Gly Ile Arg Arg Pro Trp Lys Gly Val Leu
    230                 235                 240 atg gtt ggt cca cct ggt act ggc aaa aca atg cta gca aaa gct gtt    885
Met Val Gly Pro Pro Gly Thr Gly Lys Thr Met Leu Ala Lys Ala Val
245                 250                 255                 260 gct aca gaa tgt gga aca acg ttc ttc aac gtg tct tcc tct acg ctg    933
Ala Thr Glu Cys Gly Thr Thr Phe Phe Asn Val Ser Ser Ser Thr Leu
                265                 270                 275 aca tct aaa tac aga ggc gaa tct gaa aag ctt gtc cgc ctc ttg ttt    981
Thr Ser Lys Tyr Arg Gly Glu Ser Glu Lys Leu Val Arg Leu Leu Phe
            280                 285                 290 gaa atg gcg agg ttt tac gct cca gca aca atc ttc att gat gaa att   1029
Glu Met Ala Arg Phe Tyr Ala Pro Ala Thr Ile Phe Ile Asp Glu Ile
        295                 300                 305 gat tca atc tgc agc cgc aga ggc aca tcc gat gag cac gaa gcg agt   1077
Asp Ser Ile Cys Ser Arg Arg Gly Thr Ser Asp Glu His Glu Ala Ser
    310                 315                 320 cgc aga gtc aag tca gag ctg ctt gtg caa atg gat ggg gta ggt ggt   1125
Arg Arg Val Lys Ser Glu Leu Leu Val Gln Met Asp Gly Val Gly Gly
325                 330                 335                 340 gct ttg gag aat gat gac cct tcc aag atg gtt atg gta tta gct gct   1173
Ala Leu Glu Asn Asp Asp Pro Ser Lys Met Val Met Val Leu Ala Ala
                345                 350                 355 aca aac ttt cct tgg gat att gat gaa gct ctc cga cgg aga ctg gaa   1221
Thr Asn Phe Pro Trp Asp Ile Asp Glu Ala Leu Arg Arg Arg Leu Glu
            360                 365                 370 aaa agg att tat ata cct ttg ccc aca gca aaa ggc aga gca gaa cta   1269
Lys Arg Ile Tyr Ile Pro Leu Pro Thr Ala Lys Gly Arg Ala Glu Leu
        375                 380                 385 ctt aag att aat ctt cgg gaa gta gaa ctg gat cct gac atc agc ctt   1317
Leu Lys Ile Asn Leu Arg Glu Val Glu Leu Asp Pro Asp Ile Ser Leu
    390                 395                 400 gag gaa att gct gag aag att gaa ggc tat tct ggt gct gac atc act   1365
Glu Glu Ile Ala Glu Lys Ile Glu Gly Tyr Ser Gly Ala Asp Ile Thr
405                 410                 415                 420 aat gtc tgc agg gat gcc tct tta atg gca atg aga cgg cgt att aac   1413
Asn Val Cys Arg Asp Ala Ser Leu Met Ala Met Arg Arg Arg Ile Asn
                425                 430                 435 ggc tta act cca gaa gag att cgg gca ctt tct aaa gag gaa ctt cag   1461
Gly Leu Thr Pro Glu Glu Ile Arg Ala Leu Ser Lys Glu Glu Leu Gln
            440                 445                 450 atg cca gtt acc aag ggg gac ttt gag ttg gct ctg aag aaa atc tcc   1509
Met Pro Val Thr Lys Gly Asp Phe Glu Leu Ala Leu Lys Lys Ile Ser
```

```
                455         460         465
aaa tct gtt tct gct gca gac ctg gag aag tac gag aaa tgg atg gcg    1557
Lys Ser Val Ser Ala Ala Asp Leu Glu Lys Tyr Glu Lys Trp Met Ala
    470                 475                 480 gag ttt gga tct gct taa tctcaccgac agctttccat tgtaagagtt           1605
Glu Phe Gly Ser Ala
485 ttatggctct tgttgttttc acttgcaatg tgagttagaa atcttttaa aggtttaata   1665 aaaggtctgc cgttctccct gtcccacccc caccccttcc tggtgacaag atcttttaaa  1725 ctctatttgc ctttaagggg actgaacata ataacaagct gaaacggtta aaataaaaa   1784
```

<210> SEQ ID NO 12
<211> LENGTH: 489
<212> TYPE: PRT
<213> ORGANISM: Gallus gallus

<400> SEQUENCE: 12

```
Met Asn Leu Ala Glu Ile Cys Asp Asn Ala Lys Lys Gly Arg Asp Tyr
1               5                   10                  15

Ala Leu Ile Gly Asn Tyr Asp Ser Ser Met Val Tyr Tyr Gln Gly Val
            20                  25                  30

Ile Gln Gln Ile Gln Arg His Cys Gln Ser Ile Arg Asp Pro Ala Ile
        35                  40                  45

Lys Gly Lys Trp Gln Gln Val Arg Gln Glu Leu Val Glu Glu Tyr Glu
    50                  55                  60

Gln Val Lys Ser Ile Val Asp Thr Leu Glu Ser Phe Lys Met Asp Arg
65                  70                  75                  80

Pro Ala Asp Ile Pro Val Ser Tyr Gln Asp Glu Pro Phe Arg Asp Pro
                85                  90                  95

Ala Val Trp Pro Pro Val Pro Ala Glu His Arg Ala Pro Pro Gln
            100                 105                 110

Ile Lys Arg Pro Asn Arg Gly Ala Lys Pro Leu Arg Lys Glu Ser Pro
        115                 120                 125

Gly Leu Gln Pro Arg Gly Pro Val Gly Arg Ala Gln Pro Ala Val Arg
    130                 135                 140

Ser Asp Lys Pro Ala Gly Ser Arg Asp Arg Glu Pro Arg Ala Arg Gly
145                 150                 155                 160

Arg Asp Asp Lys Gly Lys Lys Ile Pro Gln Glu Gly Val Ala Asp Asp
                165                 170                 175

Val Leu Arg Phe Asp Gly Ala Gly Tyr Asp Lys Asp Leu Val Glu Ala
            180                 185                 190

Leu Glu Arg Asp Ile Val Ser Arg Asn Pro Ser Ile His Trp Asp Asp
        195                 200                 205

Ile Ala Asp Leu Glu Glu Ala Lys Lys Leu Leu Arg Glu Ala Val Val
    210                 215                 220

Leu Pro Met Trp Met Pro Asp Phe Phe Lys Gly Ile Arg Arg Pro Trp
225                 230                 235                 240

Lys Gly Val Leu Met Val Gly Pro Pro Gly Thr Gly Lys Thr Met Leu
                245                 250                 255

Ala Lys Ala Val Ala Thr Glu Cys Gly Thr Thr Phe Phe Asn Val Ser
            260                 265                 270

Ser Ser Thr Leu Thr Ser Lys Tyr Arg Gly Glu Ser Glu Lys Leu Val
        275                 280                 285

Arg Leu Leu Phe Glu Met Ala Arg Phe Tyr Ala Pro Ala Thr Ile Phe
```

```
                290             295             300
Ile Asp Glu Ile Asp Ser Ile Cys Ser Arg Arg Gly Thr Ser Asp Glu
305             310             315             320

His Glu Ala Ser Arg Arg Val Lys Ser Glu Leu Leu Val Gln Met Asp
            325             330             335

Gly Val Gly Gly Ala Leu Glu Asn Asp Pro Ser Lys Met Val Met
            340             345             350

Val Leu Ala Ala Thr Asn Phe Pro Trp Asp Ile Asp Glu Ala Leu Arg
            355             360             365

Arg Arg Leu Glu Lys Arg Ile Tyr Ile Pro Leu Pro Thr Ala Lys Gly
            370             375             380

Arg Ala Glu Leu Leu Lys Ile Asn Leu Arg Glu Val Glu Leu Asp Pro
385             390             395             400

Asp Ile Ser Leu Glu Glu Ile Ala Glu Lys Ile Glu Gly Tyr Ser Gly
            405             410             415

Ala Asp Ile Thr Asn Val Cys Arg Asp Ala Ser Leu Met Ala Met Arg
            420             425             430

Arg Arg Ile Asn Gly Leu Thr Pro Glu Glu Ile Arg Ala Leu Ser Lys
            435             440             445

Glu Glu Leu Gln Met Pro Val Thr Lys Gly Asp Phe Glu Leu Ala Leu
            450             455             460

Lys Lys Ile Ser Lys Ser Val Ser Ala Ala Asp Leu Glu Lys Tyr Glu
465             470             475             480

Lys Trp Met Ala Glu Phe Gly Ser Ala
            485

<210> SEQ ID NO 13
<211> LENGTH: 20
<212> TYPE: DNA
<213> ORGANISM: Artificial
<220> FEATURE:
<223> OTHER INFORMATION: T3 primer

<400> SEQUENCE: 13
aattaaccct cactaaaggg                                              20

<210> SEQ ID NO 14
<211> LENGTH: 19
<212> TYPE: DNA
<213> ORGANISM: Artificial
<220> FEATURE:
<223> OTHER INFORMATION: T7 primer

<400> SEQUENCE: 14
taatacgact cactatagg                                               19

<210> SEQ ID NO 15
<211> LENGTH: 20
<212> TYPE: DNA
<213> ORGANISM: Artificial
<220> FEATURE:
<223> OTHER INFORMATION: primer sense

<400> SEQUENCE: 15
gatgaacatg aggcaagtcg                                              20

<210> SEQ ID NO 16
<211> LENGTH: 22
<212> TYPE: DNA
<213> ORGANISM: Artificial
```

<220> FEATURE:
<223> OTHER INFORMATION: primer antisense

<400> SEQUENCE: 16
ggtaacaggc atctgaagtt cc                                          22

<210> SEQ ID NO 17
<211> LENGTH: 20
<212> TYPE: DNA
<213> ORGANISM: Artificial
<220> FEATURE:
<223> OTHER INFORMATION: primer sense

<400> SEQUENCE: 17
gttcttccaa tgtggatgcc                                             20

<210> SEQ ID NO 18
<211> LENGTH: 22
<212> TYPE: DNA
<213> ORGANISM: Artificial
<220> FEATURE:
<223> OTHER INFORMATION: primer antisense

<400> SEQUENCE: 18
tcttcagaag ctcagctctt cc                                          22

<210> SEQ ID NO 19
<211> LENGTH: 20
<212> TYPE: DNA
<213> ORGANISM: Artificial
<220> FEATURE:
<223> OTHER INFORMATION: primer antisense

<400> SEQUENCE: 19
aagatggtgc aagtgacagc                                             20

<210> SEQ ID NO 20
<211> LENGTH: 20
<212> TYPE: DNA
<213> ORGANISM: Artificial
<220> FEATURE:
<223> OTHER INFORMATION: primer antisense

<400> SEQUENCE: 20
tcgatgaaga tcgtggtagg                                             20

<210> SEQ ID NO 21
<211> LENGTH: 18
<212> TYPE: DNA
<213> ORGANISM: Artificial
<220> FEATURE:
<223> OTHER INFORMATION: GAPDH primer

<400> SEQUENCE: 21
gggctgcttt taactctg                                               18

<210> SEQ ID NO 22
<211> LENGTH: 18
<212> TYPE: DNA
<213> ORGANISM: Artificial
<220> FEATURE:
<223> OTHER INFORMATION: GAPDH primer

<400> SEQUENCE: 22
ccaggaaatg agcttgac                                               18

<210> SEQ ID NO 23
<211> LENGTH: 20
<212> TYPE: DNA
<213> ORGANISM: Artificial
<220> FEATURE:
<223> OTHER INFORMATION: gapdh primer

<400> SEQUENCE: 23
cttcaccacc atggagaagg                                                  20

<210> SEQ ID NO 24
<211> LENGTH: 20
<212> TYPE: DNA
<213> ORGANISM: Artificial
<220> FEATURE:
<223> OTHER INFORMATION: gapdh primer

<400> SEQUENCE: 24
tgaagtcgca ggagacaacc                                                  20

<210> SEQ ID NO 25
<211> LENGTH: 29
<212> TYPE: DNA
<213> ORGANISM: Artificial
<220> FEATURE:
<223> OTHER INFORMATION: primer sense

<400> SEQUENCE: 25
atgaatttgg cggagatttg tgagaatgc                                        29

<210> SEQ ID NO 26
<211> LENGTH: 22
<212> TYPE: DNA
<213> ORGANISM: Artificial
<220> FEATURE:
<223> OTHER INFORMATION: primer antisense

<400> SEQUENCE: 26
tcatgcagac ccaaactcaa cc                                               22

<210> SEQ ID NO 27
<211> LENGTH: 39
<212> TYPE: DNA
<213> ORGANISM: Artificial
<220> FEATURE:
<223> OTHER INFORMATION: primer sense

<400> SEQUENCE: 27
cccggaattc atgaatttgg ctgagatttg tgataatgc                             39

<210> SEQ ID NO 28
<211> LENGTH: 38
<212> TYPE: DNA
<213> ORGANISM: Artificial
<220> FEATURE:
<223> OTHER INFORMATION: primer antisense

<400> SEQUENCE: 28
ccgccgctcg agtcaagcag atccaaattc aaccatcc                              38

<210> SEQ ID NO 29
<211> LENGTH: 491
<212> TYPE: PRT
<213> ORGANISM: Megathura crenulata

<400> SEQUENCE: 29

-continued

Ile Leu Val Arg Lys Asn Ile His Ser Leu Ser His His Glu Ala Glu
1               5                   10                  15
Glu Leu Arg Asp Ala Leu Tyr Lys Leu Gln Asn Asp Glu Ser His Gly
            20                  25                  30
Gly Tyr Glu His Ile Ala Gly Phe His Gly Tyr Pro Asn Leu Cys Pro
        35                  40                  45
Glu Lys Gly Asp Glu Lys Tyr Pro Cys Cys Val His Gly Met Ser Ile
50                  55                  60
Phe Pro His Trp His Arg Leu His Thr Ile Gln Phe Glu Arg Ala Leu
65                  70                  75                  80
Lys Lys His Gly Ser His Leu Gly Ile Pro Tyr Trp Asp Trp Thr Gln
                85                  90                  95
Thr Ile Ser Ser Leu Pro Thr Phe Phe Ala Asp Ser Gly Asn Asn Asn
            100                 105                 110
Pro Phe Phe Lys Tyr His Ile Arg Ser Ile Asn Gln Asp Thr Val Arg
        115                 120                 125
Asp Val Asn Glu Ala Ile Phe Gln Gln Thr Lys Phe Gly Glu Phe Ser
130                 135                 140
Ser Ile Phe Tyr Leu Ala Leu Gln Ala Leu Glu Glu Asp Asn Tyr Cys
145                 150                 155                 160
Asp Phe Glu Val Gln Tyr Glu Ile Leu His Asn Glu Val His Ala Leu
                165                 170                 175
Ile Gly Gly Ala Glu Lys Tyr Ser Met Ser Thr Leu Glu Tyr Ser Ala
            180                 185                 190
Phe Asp Pro Tyr Phe Met Ile His His Ala Ser Leu Asp Lys Ile Trp
        195                 200                 205
Ile Ile Trp Gln Glu Leu Gln Lys Arg Val Lys Pro Ala His Ala
210                 215                 220
Gly Ser Cys Ala Gly Asp Ile Met His Val Pro Leu His Pro Phe Asn
225                 230                 235                 240
Tyr Glu Ser Val Asn Asn Asp Asp Phe Thr Arg Glu Asn Ser Leu Pro
                245                 250                 255
Asn Ala Val Val Asp Ser His Arg Phe Asn Tyr Lys Tyr Asp Asn Leu
            260                 265                 270
Asn Leu His Gly His Asn Ile Glu Glu Leu Glu Val Leu Arg Ser
        275                 280                 285
Leu Arg Leu Lys Ser Arg Val Phe Ala Gly Phe Val Leu Ser Gly Ile
290                 295                 300
Arg Thr Thr Ala Val Val Lys Val Tyr Ile Lys Ser Gly Thr Asp Ser
305                 310                 315                 320
Asp Asp Glu Tyr Ala Gly Ser Phe Val Ile Leu Gly Gly Ala Lys Glu
                325                 330                 335
Met Pro Trp Ala Tyr Glu Arg Leu Tyr Arg Phe Asp Ile Thr Glu Thr
            340                 345                 350
Val His Asn Leu Asn Leu Thr Asp Asp His Val Lys Phe Arg Phe Asp
        355                 360                 365
Leu Lys Lys Tyr Asp His Thr Glu Leu Asp Ala Ser Val Leu Pro Ala
370                 375                 380
Pro Ile Ile Val Arg Arg Pro Asn Asn Ala Val Phe Asp Ile Ile Glu
385                 390                 395                 400
Ile Pro Ile Gly Lys Asp Val Asn Leu Pro Pro Lys Val Val Lys
            405                 410                 415

-continued

```
Arg Gly Thr Lys Ile Met Phe Met Ser Val Asp Glu Ala Val Thr Thr
            420             425             430

Pro Met Leu Asn Leu Gly Ser Tyr Thr Ala Met Phe Lys Cys Lys Val
        435             440             445

Pro Pro Phe Ser Phe His Ala Phe Glu Leu Gly Lys Met Tyr Ser Val
    450             455             460

Glu Ser Gly Asp Tyr Phe Met Thr Ala Ser Thr Thr Glu Leu Cys Asn
465             470             475             480

Asp Asn Asn Leu Arg Ile His Val His Val Asp
                485             490
```

IMMUNITY INDUCING AGENT

CROSS REFERENCE TO RELATED APPLICATIONS

This application is a Divisional of copending application Ser. No. 14/118,271, filed on Jan. 15, 2014, which was filed as PCT International Application No. PCT/JP2012/062750 on May 18, 2012, which claims the benefit under 35 U.S.C. § 119(a) to Patent Application No. 2011-112181, filed in Japan on May 19, 2011, all of which are hereby expressly incorporated by reference into the present application.

TECHNICAL FIELD

The present invention relates to a novel immunity-inducing agent useful as a therapeutic and/or prophylactic agent for cancer.

BACKGROUND ART

Cancer is the commonest cause for death among all of the causes for death, and therapies carried out therefor at present are mainly surgical treatment, which may be carried out in combination with radiotherapy and/or chemotherapy. In spite of the developments of new surgical methods and discovery of new anti-cancer agents in recent years, treatment results of cancers have not been improved very much so far except for some cancers. In recent years, by virtue of the development in molecular biology and cancer immunology, cancer antigens recognized by cytotoxic T cells reactive with cancers, as well as the genes encoding cancer antigens, were identified, and expectations for antigen-specific immunotherapies have been raised.

In immunotherapy, in order to reduce side effects, the peptide or protein to be recognized as the antigen needs to be hardly present in normal cells, and to be specifically present in cancer cells. In 1991, Boon et al. of Ludwig Institute in Belgium isolated a human melanoma antigen MAGE 1, which is recognized by CD8-positive T cells, by a cDNA-expression cloning method using an autologous cancer cell line and cancer-reactive T cells (Non-patent Document 1). Thereafter, the SEREX (serological identifications of antigens by recombinant expression cloning) method, wherein tumor antigens recognized by antibodies produced in the living body of a cancer patient in response to the patient's own cancer are identified by application of a gene expression cloning method, was reported (Patent Document 1, Non-patent Document 2), and several cancer antigens have been isolated by this method. Using a part of the cancer antigens as targets, clinical tests for cancer immunotherapy have started.

On the other hand, as in human, a number of tumors such as mammary gland tumor and squamous cell carcinoma are known in dogs and cats, and they rank high also in the statistics of diseases in dogs and cats. However, no therapeutic agent, prophylactic agent or diagnostic agent effective for cancers in dogs or cats exists at present. Since most tumors in dogs and cats are realized by their owners only after the tumors grew larger due to the progression, their visit to the hospital is already too late, and even if they receive surgical excision or administration of a human drug (an anticancer drug or the like), they often die shortly after the treatment. Under such circumstances, if therapeutic agents and prophylactic agents for cancer effective for dogs and cats become available, their uses for dog cancers are expected to be developed.

Katanin p60 subunit A-like 1 (KATNAL1) was identified as a protein having a microtubule-binding domain (Patent Document 2, Non-patent Document 3). However, there is no report suggesting that the KATNAL1 protein has immunity-inducing activity against cancer cells and hence that the protein is useful for treatment or prophylaxis of cancer.

PRIOR ART DOCUMENTS

Patent Documents

[Patent Document 1] U.S. Pat. No. 5,698,396 B
[Patent Document 2] JP 2004-8216 A

Non-Patent Documents

[Non-patent Document 1] Bruggen P. et al., Science, 254: 1643-1647 (1991)
[Non-patent Document 2] Proc. Natl. Acad. Sci. USA, 92: 11810-11813 (1995)
[Non-patent Document 3] Rigden D J. et al., FEBS Lett., March 4; 583(5): 872-8 (2009)

SUMMARY OF THE INVENTION

Problems to be Solved by the Invention

The present invention aims to discover a novel polypeptide useful for a therapeutic and/or prophylactic agent for cancer, and to provide the polypeptide for use in an immunity-inducing agent.

Means for Solving the Problems

By the SEREX method using a dog testis-derived cDNA library and serum obtained from a tumor-bearing dog, the present inventors intensively studied to obtain a cDNA encoding a protein which binds to antibodies present in serum derived from a tumor-bearing living body, and, based on the cDNA, a polypeptide of dog katanin p60 subunit A-like 1 (hereinafter referred to as KATNAL1) having the amino acid sequence of SEQ ID NO:2 was prepared. Further, based on human and mouse homologous genes of the obtained gene, human and mouse KATNAL1 having the amino acid sequences of SEQ ID NOs:4 and 6 were prepared. Further, the present inventors discovered that these KATNAL1 polypeptides are specifically expressed in tissues or cells of breast cancer, brain tumor, perianal adenocarcinoma, neuroblastoma, mastocytoma, liver cancer, prostate cancer, lung cancer, thyroid cancer and leukemia. The present inventors further discovered that administration of the KATNAL1 to a living body enables induction of immunocytes against KATNAL1 in the living body and regression of a tumor expressing KATNAL1 in the living body. Further, the present inventors discovered that a recombinant vector which can express a polynucleotide encoding the KATNAL1 polypeptide or a fragment thereof induces an antitumor effect against cancer expressing KATNAL1 in a living body.

Further, the present inventors discovered that a KATNAL1 polypeptide has a capacity to be presented by antigen-presenting cells to cause activation and the growth of cytotoxic T cells specific to the peptide (immunity-inducing activity), and therefore that the polypeptide is useful for therapy and/or prophylaxis of cancer. Further, the present inventors discovered that antigen-presenting cells which have contacted with the polypeptide, and T cells which have contacted with the antigen-presenting cells, are useful for therapy and/or prophylaxis of cancer, thereby completing the present invention.

Thus, the present invention has the following characteristics.

(1) An immunity-inducing agent comprising as an effective ingredient(s) at least one polypeptide having immunity-inducing activity selected from the polypeptides (a) to (c) below, and/or a recombinant vector(s) that comprise(s) a polynucleotide(s) encoding the at least one polypeptide, the recombinant vector(s) being capable of expressing the polypeptide(s) in vivo:

(a) a polypeptide composed of not less than 7 consecutive amino acids in any one of the amino acid sequences of SEQ ID NOs:4, 2, 8, 10 and 12 in SEQUENCE LISTING;

(b) a polypeptide having a sequence identity of not less than 85% to the polypeptide (a) and composed of not less than 7 amino acids; and (c) a polypeptide comprising the polypeptide (a) or (b) as a partial sequence thereof.

(2) The immunity-inducing agent according to (1), wherein the polypeptide having immunity-inducing activity is a polypeptide having the amino acid sequence of SEQ ID NO:4, 2, 8, 10 or 12 in SEQUENCE LISTING.

(3) The immunity-inducing agent according to (1) or (2), which is an agent for treating antigen-presenting cells.

(4) The immunity-inducing agent according to (1) or (2), which is a therapeutic and/or prophylactic agent for a cancer(s).

(5) The immunity-inducing agent according to (4), wherein the cancer(s) is/are a cancer(s) expressing KATNAL1.

(6) The immunity-inducing agent according to (4) or (5), wherein the cancer(s) is/are breast cancer, brain tumor, perianal adenocarcinoma, neuroblastoma, mastocytoma, liver cancer, prostate cancer, lung cancer, thyroid cancer and/or leukemia.

(7) The immunity-inducing agent according to any one of (1) to (6), further comprising an immunoenhancer.

(8) The immunity-inducing agent according to (7), wherein the immunoenhancer is at least one selected from the group consisting of Freund's incomplete adjuvant; Montanide; poly-I:C and derivatives thereof; CpG oligonucleotides; interleukin-12; interleukin-18; interferon-α; interferon-β; interferon-ω; interferon-γ; and Flt3 ligand.

Effect of the Invention

By the present invention, a novel immunity-inducing agent useful for therapy, prophylaxis and/or the like of cancer is provided. As concretely described in the later-mentioned Examples, administration of the polypeptide used in the present invention to a living body enables induction of immunocytes in the living body, and a cancer which has already occurred can be reduced or regressed. Therefore, the polypeptide is useful for therapy and/or prophylaxis of cancer.

BEST MODE FOR CARRYING OUT THE INVENTION

Figure 1:
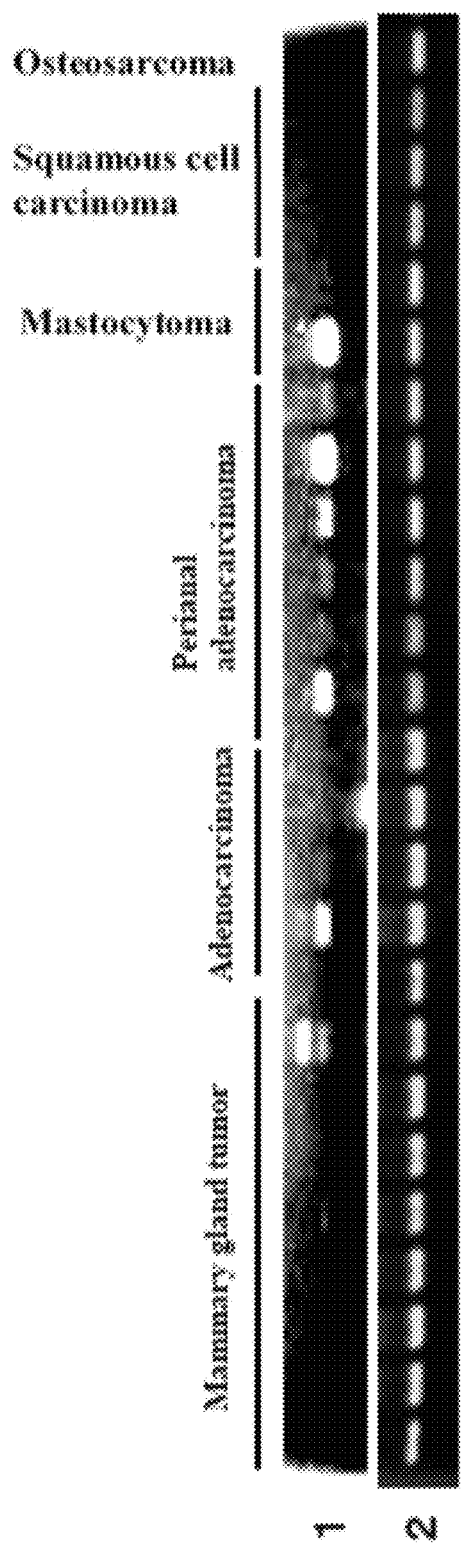
FIG. 1 shows the expression patterns of the identified KATNAL1 gene in dog normal tissues, tumor tissues and cancer cell lines. Reference numeral 1, the expression patterns of the dog KATNAL1 gene in various dog tissues and cell lines; reference numeral 2, the expression patterns of the dog GAPDH gene in various dog tissues and cell lines.

Examples of the polypeptide contained in the immunity-inducing agent of the present invention as an effective ingredient include the following. In the present invention, the term "polypeptide" means a molecule formed by a plurality of amino acids linked together by peptide bonds, and includes not only polypeptide molecules having large numbers of amino acids constituting them, but also low-molecular-weight molecules having small numbers of amino acids (oligopeptides), and full-length proteins. The present invention also includes the full-length KATNAL1 proteins having the amino acid sequence of SEQ ID NO:2, 4, 8, 10 or 12.

(a) A polypeptide that is composed of not less than 7 consecutive amino acids in a polypeptide having the amino acid sequence of SEQ ID NO:4, 2, 8, 10 or 12 in SEQUENCE LISTING, and has an immunity-inducing activity.

(b) A polypeptide composed of not less than 7 amino acids, which polypeptide has a sequence identity of not less than 85% to the polypeptide (a) and an immunity-inducing activity.

(c) A polypeptide that comprises the polypeptide (a) or (b) as a partial sequence thereof, and has an immunity-inducing activity.

In the present invention, the term "having an amino acid sequence" means that amino acid residues are arrayed in such an order. Therefore, for example, "polypeptide having the amino acid sequence of SEQ ID NO:2" means the polypeptide having the amino acid sequence of Met Asn Leu Ala . . . (snip) . . . Glu Phe Gly Ser Ala shown in SEQ ID NO:2, which polypeptide has a size of 490 amino acid residues. Further, for example, "polypeptide having the amino acid sequence of SEQ ID NO:2" may be referred to as "polypeptide of SEQ ID NO:2" for short. This also applies to the term "having a base sequence". In this case, the term "having" may be replaced with the expression "composed of".

As used herein, the term "immunity-inducing activity" means an ability to induce immunocytes that secrete cytokines such as interferon in a living body.

Whether or not the polypeptide has an immunity-inducing activity can be confirmed using, for example, the known ELISPOT assay. More specifically, for example, as described in the Examples below, cells such as peripheral blood mononuclear cells are obtained from a living body subjected to administration of the polypeptide whose immunity-inducing activity is to be evaluated, and the obtained cells are then cocultured with the polypeptide, followed by measuring the amount(s) of a cytokine(s) produced by the cells using a specific antibody/antibodies, thereby enabling measurement of the number of immunocytes among the cells. By this, evaluation of the immunity-inducing activity is possible.

Alternatively, as described in the later-mentioned Examples, administration of the recombinant polypeptide of any of (a) to (c) described above to a tumor-bearing animal allows regression of the tumor by its immunity-inducing activity. Thus, the above immunity-inducing activity can be evaluated also as an ability to suppress the growth of cancer cells or to cause reduction or disappearance of a cancer tissue (tumor) (hereinafter referred to as "antitumor activity"). The antitumor activity of a polypeptide can be confirmed by, for example, as more specifically described in the Examples below, observation of whether or not a tumor is reduced when the polypeptide was actually administered to a tumor-bearing living body.

Alternatively, the antitumor activity of a polypeptide can be evaluated also by observation of whether or not T cells stimulated with the polypeptide (that is, T cells brought into contact with antigen-presenting cells presenting the polypeptide) show a cytotoxic activity against tumor cells in vitro. The contact between the T cells and the antigen-presenting cells can be carried out by their coculture in a liquid medium, as mentioned below. Measurement of the cytotoxic activity can be carried out by, for example, the known method called $^{51}$Cr release assay described in Int. J. Cancer, 58: p 317, 1994. In cases where the polypeptide is to be used for therapy and/or prophylaxis of cancer, the evaluation of the immunity-inducing activity is preferably carried out using the antitumor activity as an index, although the index is not limited thereto.

Each of the amino acid sequences of SEQ ID NOs:2, 4, 8, 10 and 12 in SEQUENCE LISTING disclosed in the present invention is an amino acid sequence of KATNAL1 protein that was isolated, by the SEREX method using a dog testis-derived cDNA library and serum of a tumor-bearing dog, as a polypeptide that specifically binds to an antibody existing in the serum of a tumor-bearing dog, or a homologous factor of the polypeptide in human, cow, horse or chicken (see Example 1). Human KATNAL1, which is the human homologous factor of dog KATNAL1, has a sequence identity of 95% in terms of the base sequence and 98% in terms of the amino acid sequence; bovine KATNAL1, which is the bovine homologous factor, has a sequence identity of 91% in terms of the base sequence and 97% in terms of the amino acid sequence; equine KATNAL1, which is the equine homologous factor, has a sequence identity of 87% in terms of the base sequence and 88% in terms of the amino acid sequence; and chicken KATNAL1, which is the chicken homologous factor, has a sequence identity of 81% in terms of the base sequence and 90% in terms of the amino acid sequence.

The polypeptide (a) is a polypeptide composed of not less than 7 consecutive, preferably 8, 9 or not less than 10 consecutive, amino acids in the polypeptide having the amino acid sequence of SEQ ID NO:2, 4, 8, 10 or 12, and has an immunity-inducing activity. The polypeptide is more preferably a polypeptide composed of an amino acid sequence having a sequence identity of not less than 85% to the amino acid sequence of SEQ ID NO:4, and the polypeptide especially preferably has the amino acid sequence of SEQ ID NO:2, 4, 8, 10 or 12. As is known in the art, a polypeptide having not less than about 7 amino acid residues can exert its antigenicity and immunogenicity. Thus, a polypeptide having not less than 7 consecutive amino acid residues in the amino acid sequence of SEQ ID NO:2 or 4 can have an immunity-inducing activity, so that the polypeptide can be used for preparation of the immunity-inducing agent of the present invention.

As a principle of immune induction by administration of a cancer antigenic polypeptide, the following process is known: a polypeptide is incorporated into an antigen-presenting cell and then degraded into smaller fragments by peptidases in the cell, followed by being presented on the surface of the cell. The fragments are then recognized by a cytotoxic T cell or the like that selectively kills cells presenting the antigen. The size of the polypeptide presented on the surface of the antigen-presenting cell is relatively small and about 7 to 30 amino acids. Therefore, from the viewpoint of presenting the polypeptide on the surface of the antigen-presenting cell, one preferred mode of the above-described polypeptide (a) is a polypeptide composed of about 7 to 30 consecutive amino acids in the amino acid sequence of SEQ ID NO:2, 4, 8, 10 or 12, and more preferably, a polypeptide composed of about 8 to 30 or about 9 to 30 amino acids is sufficient as the polypeptide (a). In some cases, these relatively small polypeptides are presented directly on the surface of antigen-presenting cells without being incorporated into the antigen-presenting cells.

Further, a polypeptide incorporated into an antigen-presenting cell is cleaved at random sites by peptidases in the cell to yield various polypeptide fragments, which are then presented on the surface of the antigen-presenting cell. Therefore, administration of a large polypeptide such as the full-length region of SEQ ID NO:2, 4, 8, 10 or 12 inevitably causes production of polypeptide fragments by degradation in the antigen-presenting cell, which fragments are effective for immune induction via the antigen-presenting cell. Therefore, also for immune induction via antigen-presenting cells, a large polypeptide can be preferably used, and the polypeptide may be composed of not less than 30, preferably not less than 100, more preferably not less than 200, still more preferably not less than 250 amino acids. The polypeptide may be still more preferably composed of the full-length region of SEQ ID NO:2, 4, 8, 10 or 12.

The polypeptide (b) is the same polypeptide as the polypeptide (a) except that a small number of (preferably, one or several) amino acid residues are substituted, deleted and/or inserted, which has a sequence identity of not less than 90%, preferably not less than 95%, more preferably not less than 98%, still more preferably not less than 99% or not less than 99.5% to the original sequence and has an immunity-inducing activity. It is well known in the art that, in general, there are cases where a protein antigen retains almost the same antigenicity as the original protein even if the amino acid sequence of the protein is modified such that a small number of amino acid residues are substituted, deleted and/or inserted. Therefore, since the polypeptide (b) may also exert an immunity-inducing activity, it can be used for preparation of the immunity-inducing agent of the present invention. Further, the polypeptide (b) is also preferably a polypeptide having the same amino acid sequence as the amino acid sequence of SEQ ID NO:2, 4, 8, 10 or 12 except that one or several amino acid residues are substituted, deleted and/or inserted. As used herein, the term "several" means an integer of 2 to 10, preferably an integer of 2 to 6, more preferably an integer of 2 to 4.

As used herein, the term "sequence identity" of amino acid sequences or base sequences means the value calculated by aligning two amino acid sequences (or base sequences) to be compared such that the number of matched amino acid residues (or bases) is maximum between the amino acid sequences (or base sequences), and dividing the number of matched amino acid residues (or the number of matched bases) by the total number of amino acid residues (or the total number of bases), which value is represented as a percentage. When the alignment is carried out, one or more gaps are inserted into one or both of the two sequences to be compared as required. Such alignment of sequences can be carried out using a well-known program such as BLAST, FASTA or CLUSTAL W. When one or more gaps are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The 20 types of amino acids constituting naturally occurring proteins may be classified into groups in each of which similar properties are shared, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in many cases, substitution of an amino acid within the same group does not change the properties of the polypeptide. Therefore, in cases where an amino acid residue in the polypeptide (a) of the present invention is substituted, the probability that the immunity-inducing activity can be maintained may be increased by carrying out the substitution within the same group, which is preferred.

The polypeptide (c) is a polypeptide that comprises the polypeptide (a) or (b) as a partial sequence and has an immunity-inducing activity. That is, the polypeptide (c) is a polypeptide in which one or more amino acids and/or one or more polypeptides is added at one or both ends of the polypeptide (a) or (b), and has an immunity-inducing activity. Such a polypeptide can also be used for preparation of the immunity-inducing agent of the present invention.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques by preparing a polynucleotide encoding the polypeptide and incorporating the polynucleotide into an expression vector, followed by introducing the resulting vector into a host cell and allowing the host cell to produce the polypeptide therein.

The polynucleotide encoding the above polypeptide can be easily prepared by a known genetic engineering technique or a conventional method using a commercially available nucleic acid synthesizer. For example, DNA having the base sequence of SEQ ID NO:1 can be prepared by carrying out PCR using a dog chromosomal DNA or cDNA library as a template, and a pair of primers designed such that the base sequence of SEQ ID NO:1 can be amplified therewith. DNA having the base sequence of SEQ ID NO:3 can be similarly prepared by using a human chromosomal DNA or cDNA library as the template. The reaction conditions for the PCR can be set appropriately, and examples of the reaction conditions include, but are not limited to, repeating the reaction process of 94° C. for 30 seconds (denaturation), 55° C. for 30 seconds to 1 minute (annealing) and 72° C. for 2 minutes (extension) for, for example, 30 cycles, followed by the reaction at 72° C. for 7 minutes. Further, the desired DNA can be isolated by preparing an appropriate probe or primer based on the information of the base sequence or the amino acid sequence of SEQ ID NO:1 or 3 in SEQUENCE LISTING in the present description, and screening a cDNA library of dog, human or the like using the probe or primer. The cDNA library is preferably prepared from cells, an organ or a tissue expressing the protein of SEQ ID NO:2 or 4. The above-described operations such as preparation of the probe or primer, construction of the cDNA library, screening of the cDNA library and cloning of the gene of interest are known to those skilled in the art, and can be carried out according to the methods described in Molecular Cloning, Second Edition; Current Protocols in Molecular Biology; and/or the like. From the thus obtained DNA, DNA encoding the polypeptide (a) can be obtained. Further, since the codons encoding each amino acid are known, the base sequence of a polynucleotide encoding a specific amino acid sequence can be easily specified. Therefore, since the base sequence of a polynucleotide encoding the polypeptide (b) or polypeptide (c) can also be easily specified, such a polynucleotide can also be easily synthesized using a commercially available nucleic acid synthesizer according to a conventional method.

The host cells are not restricted as long as the cells can express the above-described polypeptide, and examples of the cells include, but are not limited to, prokaryotic cells such as *E. coli*; and eukaryotic cells such as mammalian cultured cells including monkey kidney cells COS 1 and Chinese hamster ovary cells CHO; budding yeast; fission yeast; silkworm cells; and *Xenopus laevis* egg cells.

In cases where prokaryotic cells are used as the host cells, an expression vector containing an origin that enables replication of the vector in a prokaryotic cell, promoter, ribosome binding site, DNA cloning site, terminator and/or the like is used. Examples of the expression vector for *E. coli* include the pUC system, pBluescriptII, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In such a case, the polypeptide can also be expressed as a fusion protein with another protein.

In cases where eukaryotic cells are used as the host cells, an expression vector for eukaryotic cells, comprising a promoter, splicing site, poly(A) addition site and/or the like is used as the expression vector. Examples of such an expression vector include pKA1, pCDM8, pSVK3, pMSG, pSVL, pBK-CMV, pBK-RSV, EBV vector, pRS, pcDNA3, pMSG and pYES2. Similarly to the above case, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pINDN5-His, pFLAG-CMV-2, pEGFP-N1, pEGFP-C1 or the like is used as the expression vector, the above polypeptide can be expressed as a fusion protein comprising a tag such as a His tag, FLAG tag, myc tag, HA tag or GFP.

For the introduction of the expression vector into host cells, a well-known method such as electroporation, the calcium phosphate method, the liposome method or the DEAE dextran method may be used.

Isolation and purification of the polypeptide of interest from the host cells can be carried out by a combination of known separation operations. Examples of the known separation operations include, but are not limited to, treatment with a denaturant such as urea or with a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above methods also include, as mentioned above, those in the form of a fusion protein with another arbitrary protein. Examples of such polypeptides include fusion proteins with glutathion S-transferase (GST) and fusion proteins with a His tag. Such a polypeptide in the form of a fusion protein is also included within the scope of the present invention as the above-described polypeptide (c). Further, in some cases, the polypeptide expressed in a transformed cell is modified in various ways in the cell after translation. Such a post-translationally modified polypeptide is also included within the scope of the present invention as long as it has an immunity-inducing activity. Examples of such a post-translational modification include: elimination of N-terminal methionine; N-terminal acetylation; glycosylation; limited degradation by an intracellular protease; myristoylation; isoprenylation; and phosphorylation.

As described more concretely in the later-mentioned Examples, administration of the polypeptide having an immunity-inducing activity to a tumor-bearing living body enables regression of an already existing tumor. Therefore, the immunity-inducing agent of the present invention can be used as a therapeutic and/or prophylactic agent for cancer. Further, the polypeptide having an immunity-inducing activity can be used for a method of therapy and/or prophylaxis of cancer by immune induction.

As used herein, the terms "tumor" and "cancer" mean a malignant neoplasm, and are used interchangeably In this case, the cancer to be treated is not restricted as long as the gene encoding the polypeptide of SEQ ID NO:KATNAL1 is expressed in the cancer, and the cancer is preferably breast cancer, brain tumor, perianal adenocarcinoma, neuroblastoma, mastocytoma, liver cancer, prostate cancer, lung cancer, thyroid cancer or leukemia.

The subject animal is preferably a mammal, more preferably a mammal such as a primate, pet animal, domestic animal or sport animal, especially preferably human, dog or cat.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of cancer, it may be administered to a regional lymph node in the vicinity of the tumor to be treated, as described in the Examples below, in order to enhance its anticancer activity. The dose may be any dose as long as the dose is effective for immune induction, and, for example, in cases where the agent is used for therapy and/or prophylaxis of cancer, the dose may be one effective for therapy and/or prophylaxis of the cancer. The dose effective for therapy and/or prophylaxis of cancer is appropriately selected depending on the size, symptoms and the like of the tumor, and the effective dose is usually 0.0001 μg to 1000 μg, preferably 0.001 μg to 1000 μg per subject animal per day. The agent may be administered once, or dividedly in several times. The agent is preferably administered dividedly in several times, every several days to several months. As concretely shown in the Examples below, the immunity-inducing agent of the present invention can cause regression of an already occurred tumor. Therefore, since the agent can exert its anticancer activity also against a small number of cancer cells at an early stage, development or recurrence of cancer can be prevented by using the agent before development of the cancer or after therapy for the cancer. That is, the immunity-inducing agent of the present invention is effective for both therapy and prophylaxis of cancer.

The immunity-inducing agent of the present invention may contain only a polypeptide or may be formulated by being mixed as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additives include, but are not limited to, diluents such as physiological buffer solutions; vehicles such as sugar, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the immunoenhancer include adjuvants. Adjuvants can enhance the immune response by providing a reservoir of antigen (extracellularly or inside macrophages), activating macrophages and stimulating specific sets of lymphocytes, thereby enhancing the immune response and hence the anticancer action. Therefore, especially in cases where the immunity-inducing agent of the present invention is used for therapy and/or prophylaxis of cancer, the immunity-inducing agent preferably comprises an adjuvant, in addition to the above-described polypeptide as an effective ingredient. Many types of adjuvants are well known in the art, and any of these adjuvants may be used. Specific examples of the adjuvants include MPL (SmithKline Beecham), homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in PCT application WO 96/33739 (SmithKline Beecham); QS-7, QS-17, QS-18 and QS-L1 (So and 10 colleagues, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 colleagues, Nature, Vol. 374, p. 546-549); poly-I:C and derivatives thereof (e.g., poly ICLC); and various water-in-oil emulsions prepared from biodegradable oils such as squalene and/or tocopherol. Among these, Freund's incomplete adjuvant; Montanide; poly-I:C and derivatives thereof; and CpG oligonucleotides are preferred. The mixing ratio between the above-described adjuvant and the polypeptide is typically about 1:10 to 10:1, preferably about 1:5 to 5:1, more preferably about 1:1. However, the adjuvant is not limited to the above-described examples, and adjuvants known in the art other than those described above may also be used when the immunity-inducing agent of the present invention is administered (see, for example, Goding, "Monoclonal Antibodies: Principles and Practice, 2nd edition", 1986). Preparation methods for mixtures or emulsions of a polypeptide and an adjuvant are well known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples of the cytokines include, but are not limited to, interleukin-12 (IL-12), GM-CSF, IL-18, interferon-α, interferon-β, interferon-ω, interferon-γ, and Flt3 ligand, which have been shown to enhance the prophylactic action of vaccines. Such factors may also be used as the above-described immunoenhancer, and may be contained in the immunity-inducing agent of the present invention, or may be prepared as a separate composition to be administered to a patient in combination with the immunity-inducing agent of the present invention.

By bringing the above-described polypeptide into contact with antigen-presenting cells in vitro, the antigen-presenting cells can be made to present the polypeptide. That is, the polypeptides (a) to (c) described above can be used as agents for treating antigen-presenting cells. Examples of the antigen-presenting cells which may be preferably used include dendritic cells and B cells having MHC class I molecules. Various MHC class I molecules have been identified and are well-known. MHC molecules in human are called HLA. Examples of HLA class I molecules include HLA-A, HLA-B and HLA-C, more specifically, HLA-Al, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

By administering an effective amount of such dendritic cells, a response desired for therapy of a cancer can be induced. As the cells, bone marrow or umbilical cord blood donated by a healthy individual, or bone marrow, peripheral blood or the like of the patient may be used. When autologous cells of the patient are used, high safety can be attained and serious side effects are expected to be avoided. The peripheral blood or bone marrow may be any of a fresh sample, cold-stored sample and cryopreserved sample. As for the peripheral blood, whole blood may be cultured or the leukocyte components alone may be separated and cultured, and the latter is more efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. The production method for the cytokine is not restricted, and a naturally-occurring or recombinant cytokine or the like may be employed as long as its safety and physiological activity have been confirmed. Preferably, a preparation with assured quality for medical use is used in the minimum necessary amount. The concentration of the cytokine(s) to be added is not restricted as long as the dendritic cells are induced at the concentration, and usually, the total concentration of the cytokine(s) is preferably about 10 to 1000 ng/mL, more preferably about 20 to 500 ng/mL. The culture may be carried out using a well-known medium usually used for culture of leukocytes. The culturing temperature is not restricted as long as proliferation of leukocytes is possible at the temperature, and a temperature of about 37° C., which is the body temperature of human, is most preferred. The atmospheric environment during the culture is not restricted as long as proliferation of the leukocytes is possible under the environment, and the culture is preferably performed under a flow of 5% $CO_2$. The culturing period is not restricted as long as a necessary number of the cells are induced, and usually 3 days to 2 weeks. As for the apparatuses used for separation and culturing of the cells, appropriate apparatuses, preferably those whose safety upon application to medical uses have been confirmed and whose operations are stable and simple, may be employed. In particular, examples of the cell-culturing apparatus include not only general vessels such as Petri dishes, flasks and bottles, but also layer-type vessels, multistage vessels, roller bottles, spinner-type bottles, bag-type culturing vessels and hollow fiber columns.

The method per se to be used for bringing the above-described polypeptide into contact with the antigen presenting cells in vitro may be those well known in the art. For example, the antigen-presenting cells may be cultured in a culture medium containing the above-described polypeptide. The concentration of the peptide in the medium is not restricted, and usually about 1 to 100 μg/ml, preferably about 5 to 20 μg/ml. The cell density during the culture is not restricted and usually about $10^3$ to $10^7$ cells/ml, preferably about $5 \times 10^4$ to $5 \times 10^6$ cells/ml. The culture is preferably carried out according to a conventional method at 37° C. under the atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues, although the length is not restricted.

By culturing the antigen-presenting cells in the coexistence of the above-described polypeptide, the polypeptide is incorporated into MHC molecules of the antigen-presenting cells and presented on the surface of the antigen-presenting cells. Therefore, using the above-described polypeptide, isolated antigen-presenting cells containing the complex between the polypeptide and the MHC molecule can be prepared. Such antigen-presenting cells can present the polypeptide against T cells in vivo or in vitro, to induce, and allow proliferation of, cytotoxic T cells specific to the polypeptide.

By bringing the thus prepared antigen-presenting cells having the complex between the above-described polypeptide and the MHC molecule into contact with T cells in vitro, cytotoxic T cells specific to the polypeptide can be induced and allowed to proliferate. This may be carried out by coculturing the above-described antigen-presenting cells and T cells in a liquid medium. For example, the antigen-presenting cells may be suspended in a liquid medium and placed in a vessel such as a well of a microplate, followed by adding T cells to the well and then performing culture. The mixing ratio of the antigen-presenting cells to the T cells in the coculture is not restricted, and usually about 1:1 to 1:100, preferably about 1:5 to 1:20 in terms of the cell number. The density of the antigen-presenting cells to be suspended in the liquid medium is not restricted, and usually about 100 to 10,000,000 cells/ml, preferably about 10,000 to 1,000,000 cells/ml. The coculture is preferably carried out by a conventional method at 37° C. under the atmosphere of 5% $CO_2$. The culturing period is not restricted, and usually 2 days to 3 weeks, preferably about 4 days to 2 weeks. The coculture is preferably carried out in the presence of one or more interleukins such as IL-2, IL-6, IL-7 and/or IL-12. In such cases, the concentration of IL-2 or IL-7 is usually about 5 to 20 U/ml, the concentration of IL-6 is usually about 500 to 2000 U/ml, and the concentration of IL-12 is usually about 5 to 20 ng/ml, but the concentrations of the interleukins are not restricted thereto. The above coculture may be repeated once to several times with addition of fresh antigen-presenting cells. For example, the operation of discarding the culture supernatant after the coculture and adding a fresh suspension of antigen-presenting cells to further conduct the coculture may be repeated once to several times. The conditions for each coculture may be the same as those described above.

By the above-described coculture, cytotoxic T cells specific to the polypeptide are induced and allowed to proliferate. Thus, using the above-described polypeptide, isolated T cells can be prepared which selectively bind to the complex between the polypeptide and the MHC molecule.

As described in the Examples below, the KATNAL1 gene is expressed specifically in breast cancer cells, breast cancer tissues, brain tumor cells, brain tumor tissues, perianal adenocarcinoma tissues, perianal adenocarcinoma cells, mastocytoma tissues, mastocytoma cells, neuroblastoma cells, liver cancer cells, liver cancer tissues, prostate cancer cells, prostate cancer tissues, lung cancer cells, lung cancer tissues, thyroid cancer cells, thyroid cancer tissues, and leukemia cells. Therefore, it is thought that, in these cancer species, a significantly larger amount of KATNAL1 exists than in normal cells. Therefore, when a part of the KATNAL1 polypeptide present in cancer cells is presented by MHC molecules on the surface of the cancer cells, and the thus prepared cytotoxic T cells are administered to the living body, the cytotoxic T cells can damage the cancer cells using the presented polypeptide as a marker. Since the antigen-presenting cells presenting the above-described polypeptide can induce, and allow proliferation of, cytotoxic T cells specific to the polypeptide also in vivo, cancer cells can be damaged also by administering the antigen-presenting cells to a living body. That is, the cytotoxic T cells and the antigen-presenting cells prepared using the polypeptide are also effective as therapeutic and/or prophylactic agents for cancer, similarly to the immunity-inducing agent of the present invention.

In cases where the above-described isolated antigen-presenting cells or isolated T cells are administered to a living body, these are preferably prepared by treating antigen presenting cells or T cells collected from the patient to be treated, using the polypeptide (a), (b) or (c) as described above in order to avoid the immune response in the living body that attacks these cells as foreign bodies.

The therapeutic and/or prophylactic agent for cancer comprising as an effective ingredient the antigen-presenting cells or T cells is preferably administered via a parenteral administration route, for example, by intravenous or intraarterial administration. The dose is appropriately selected depending on the symptoms, the purpose of administration and the like, and is usually 1 cell to 10,000,000,000,000 cells, preferably 1,000,000 cells to 1,000,000,000 cells, which dose is preferably administered once every several days to once every several months. The formulation may be, for example, the cells suspended in physiological buffered saline, and the formulation may be used in combination with another/other anticancer preparation(s) and/or cytokine(s). Further, one or more additives well known in the field of formulation of pharmaceuticals may also be added.

Also by expressing a polynucleotide encoding any of the polypeptides (a) to (c) in the body of the subject animal, antibody production and cytotoxic T cells can be induced in the living body, and an effect comparable to that obtained in the case of administration of the polypeptide can be obtained. That is, the immunity-inducing agent of the present invention may be one comprising as an effective ingredient a recombinant vector having a polynucleotide encoding any of the polynucleotides (a) to (c), which recombinant vector is capable of expressing the polypeptide in a living body. Such a recombinant vector capable of expressing an antigenic polypeptide as shown in the later-mentioned Examples is also called a gene vaccine.

The vector used for production of the gene vaccine is not restricted as long as it is a vector capable of expressing the polypeptide in a cell of the subject animal (preferably in a mammalian cell), and may be either a plasmid vector or a virus vector, and any known vector in the field of gene vaccines may be used. The polynucleotide such as DNA or RNA encoding the above-described polypeptide can be easily prepared as mentioned above by a conventional method. Incorporation of the polynucleotide into the vector can be carried out using a method well known to those skilled in the art.

The administration route of the gene vaccine is preferably a parenteral route such as intramuscular, subcutaneous, intravenous or intraarterial administration. The dose may be appropriately selected depending on the type of the antigen and the like, and is usually about 0.1 μg to 100 mg, preferably about 1 μg to 10 mg in terms of the weight of the gene vaccine per kg body weight.

Examples of the method using a virus vector include those wherein a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), and the liposome method, lipofectin method, microinjection method, calcium phosphate method and electroporation method. The DNA vaccine method and liposome method are especially preferred.

Methods for making the gene encoding the above-described polypeptide used in the present invention actually act as a pharmaceutical include in vivo methods wherein the gene is directly introduced into the body, and ex vivo methods wherein a certain kind of cells are collected from the subject animal and the gene is then introduced into the cells ex vivo, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these literatures, and the like). The in vivo methods are more preferred.

In cases where the gene is administered by an in vivo method, the gene may be administered through an appropriate administration route depending on the disease to be treated, symptoms and the like. The gene may be administered by, for example, intravenous, intraarterial, subcutaneous or intramuscular administration. In cases where the gene is administered by an in vivo method, the gene may be formulated into a preparation such as a solution, and in general, it is formulated into an injection solution or the like containing DNA encoding the above-described peptide of the present invention as an effective ingredient. A commonly used carrier may be also added thereto as required. In cases of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence of SEQ ID NO:1" includes not only the actual base sequence of SEQ ID NO:1, but also the sequence complementary thereto. Thus, "the polynucleotide having the base sequence of SEQ ID NO:1" includes the single-stranded polynucleotide having the actual base sequence of SEQ ID NO:1, the single-stranded polynucleotide having the base sequence complementary thereto, and the double-stranded polynucleotide composed of these single-stranded polynucleotides. When a polynucleotide encoding the polypeptide used in the present invention is prepared, any one of these base sequences is appropriately selected, and those skilled in the art can easily carry out the selection.

EXAMPLES

The present invention will now be described more concretely by way of Examples.

Example 1

Obtaining Novel Cancer Antigen Protein by SEREX Method (1) Preparation of cDNA Library Total RNA was extracted from testis of a dog by the acid-guanidium-phenol-chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a cDNA phage library was synthesized. For the preparation of a cDNA phage library, cDNA Synthesis Kit, Zap-cDNA Synthesis Kit, and ZAP-cDNA Gigapack III Gold Cloning Kit (manufactured by STRATAGENE) were used in accordance with the protocols attached to the kits. The size of the prepared cDNA phage library was $1 \times 10^6$ pfu/ml.

(2) Screening of cDNA Library with Serum

Using the thus prepared cDNA phage library, immunoscreening was carried out. More specifically, the host E. coli (XL1-Blue MRF') was infected with the library such that 2340 clones appeared on an NZY agarose plate with a size of 90 mm dia.×15 mm, and cultured at 42° C. for 3 to 4 hours to allow the phage to form plaques. The plate was covered with a nitrocellulose membrane (Hybond C Extra: manufactured by GE Healthcare Bio-Science) impregnated with IPTG (isopropyl-β-D-thiogalactoside) at 37° C. for 4 hours to allow induction and expression of proteins, and the proteins were transferred onto the membrane. Subsequently, the membrane was recovered and soaked in TBS (10 mM Tris-HCl, 150 mM NaCl; pH 7.5) supplemented in 0.5% non-fat dry milk. The membrane was then shaken at 4° C. overnight to suppress non-specific reactions. This filter was then allowed to react with 500-fold diluted dog patient serum at room temperature for 2 to 3 hours.

As the above-described dog patient serum, serum collected from a dog patient with a perianal tumor was used. The serum was stored at −80° C. and pretreated immediately before use. The method of the pretreatment of serum was as follows. That is, the host E. coli (XL1-Blue MRF') was infected with λ ZAP Express phage having no foreign gene inserted, and then cultured on NZY plate medium at 37° C. overnight. Subsequently, 0.2 M NaHCO$_3$ buffer (pH 8.3) supplemented with 0.5 M NaCl was added to the plate, and the plate was left to stand at 4° C. for 15 hours, followed by collecting the supernatant as an E. coli/phage extract. Thereafter, the collected E. coli/phage extract was passed through an NHS-column (manufactured by GE Healthcare Bio-Science) to immobilize proteins derived from the E. coli/phage thereon. The serum from the dog patient was passed through, and reacted with, this protein-immobilized column to remove antibodies that adsorb to E. coli and/or the phage. The serum fraction that passed through the column was 500-fold diluted with TBS supplemented with 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and reacted with goat anti-dog IgG (Goat anti Dog IgG-h+l HRP conjugated: manufactured by BETHYL Laboratories) 5,000-fold diluted with TBS supplemented with 0.5% non-fat dry milk as a secondary antibody at room temperature for 1 hour, followed by detection by enzyme coloring reaction using an NBT/BCIP reaction solution (manufactured by Roche). Colonies at positions corresponding to coloring-reaction-positive sites were recovered from the NZY agarose plate having a size of 90 mm dia.×15 mm, and dissolved in 500 μl of SM buffer (100 mM NaCl, 10 mM MgClSO$_4$, 50 mM Tris-HCl, 0.01% gelatin; pH 7.5). The screening was repeated as the second and third screening in the same manner as described above until a single coloring-reaction-positive colony was obtained. The isolation of the single positive clone was achieved after screening of 9110 phage clones reactive with IgG in the serum.

(3) Sequence Homology Search of Isolated Antigen Gene

To subject the single positive clone isolated by the above-described method to base sequence analysis, an operation of conversion of the phage vector to a plasmid vector was carried out. More specifically, 200 μl of a solution prepared such that the host E. coli (XL1-Blue MRF') was contained at an absorbance OD$_{600}$ of 1.0 was mixed with 100 μl of a purified phage solution and further with 1 μl of ExAssist helper phage (manufactured by STRATAGENE), and the reaction was then allowed to proceed at 37° C. for 15 minutes. This was followed by addition of 3 ml of LB medium to the reaction mixture, and culture was performed with the resulting mixture at 37° C. for 2.5 to 3 hours. The resulting culture was immediately incubated in a water bath at 70° C. for 20 minutes. The culture was then centrifuged at 4° C. at 1,000×g for 15 minutes, and the supernatant was recovered as a phagemid solution. Subsequently, 200 µl of a solution prepared such that the phagemid host *E. coli* (SOLR) was contained at an absorbance OD$_{600}$ of 1.0 was mixed with 10 µl of a purified phage solution, and the reaction was allowed to proceed at 37° C. for 15 minutes. Thereafter, 50 µl of the reaction mixture was plated on LB agar medium supplemented with ampicillin (final concentration: 50 µg/ml), and culture was performed at 37° C. overnight. A single colony of transformed SOLR was recovered and cultured in LB medium supplemented with ampicillin (final concentration: 50 µg/ml) at 37° C., followed by purification of plasmid DNA having the insert of interest using QIAGEN plasmid Miniprep Kit (manufactured by Qiagen).

The purified plasmid was subjected to analysis of the full-length sequence of the insert by the primer walking method using the T3 primer of SEQ ID NO:13 and the T7 primer of SEQ ID NO:14. By this sequence analysis, the gene sequence of SEQ ID NO:1 was obtained. Using the base sequence and the amino acid sequence of this gene, homology search against known genes was carried out using a sequence homology search program BLAST. As a result, it was revealed that the obtained gene is the KATNAL1 gene. Human KATNAL1, which is a human homologous factor of dog KATNAL1, had a sequence identity of 95% in terms of the base sequence and 98% in terms of the amino acid sequence; mouse KATNAL1, which is a mouse homologous factor, had a sequence identity of 85% in terms of the base sequence and 94% in terms of the amino acid sequence; bovine KATNAL1, which is a bovine homologous factor, had a sequence identity of 91% in terms of the base sequence and 97% in terms of the amino acid sequence; equine KATNAL1, which is an equine homologous factor, had a sequence identity of 87% in terms of the base sequence and 88% in terms of the amino acid sequence; and chicken KATNAL1, which is a chicken homologous factor, had a sequence identity of 81% in terms of the base sequence and 90% in terms of the amino acid sequence. The base sequence and the amino acid sequence of human KATNAL1 are shown in SEQ ID NO:3 and SEQ ID NO:4, respectively; the base sequence and the amino acid sequence of mouse KATNAL1 are shown in SEQ ID NO:5 and SEQ ID NO:6, respectively; the base sequence and the amino acid sequence of bovine KATNAL1 are shown in SEQ ID NO:7 and SEQ ID NO:8, respectively; the base sequence and the amino acid sequence of equine KATNAL1 are shown in SEQ ID NO:9 and SEQ ID NO:10, respectively; and the base sequence and the amino acid sequence of chicken KATNAL1 are shown in SEQ ID NO:11 and SEQ ID NO:12, respectively.

(4) Analysis of Expression in Various Tissues

Figure 2:
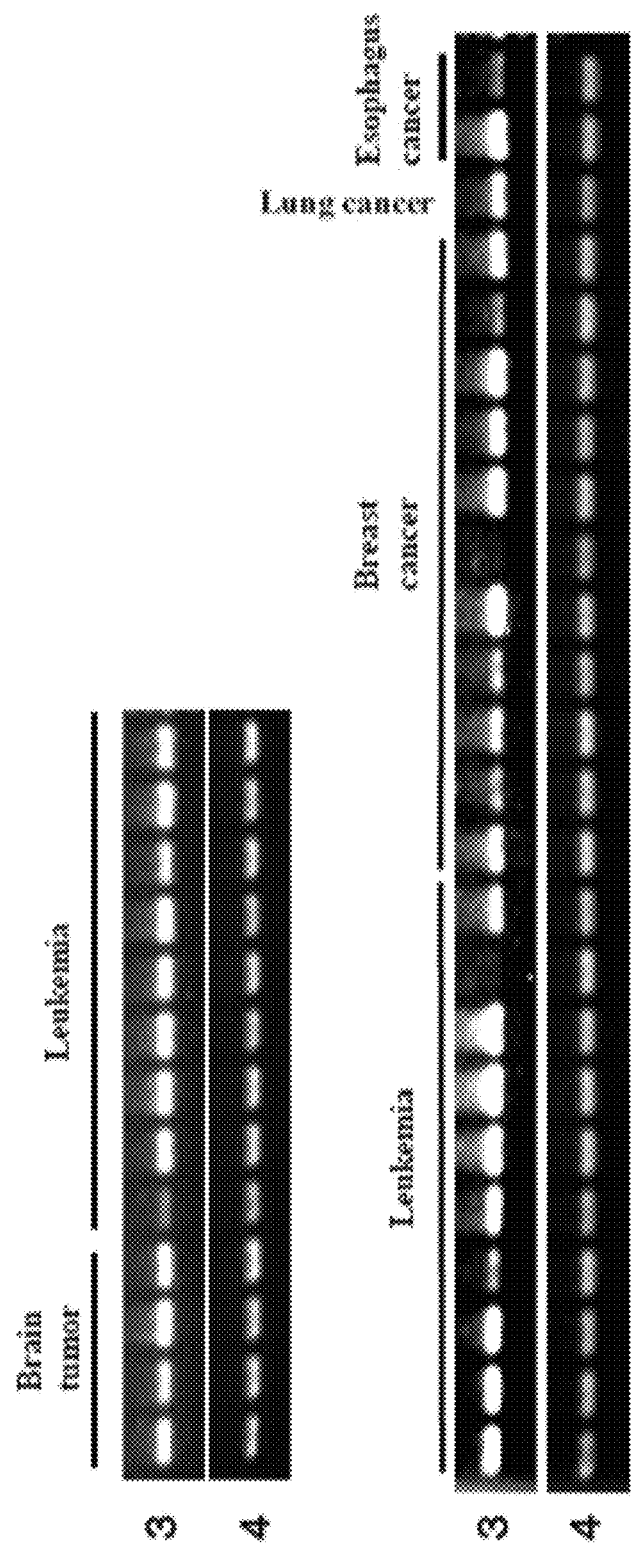
FIG. 2 shows the expression patterns of the identified KATNAL1 gene in human normal tissues, tumor tissues and cancer cell lines. Reference numeral 3, the expression patterns of the human KATNAL1 gene in various human tissues and cell lines; reference numeral 4, the expression patterns of the human GAPDH gene in various human tissues and cell lines.
Figure 3:
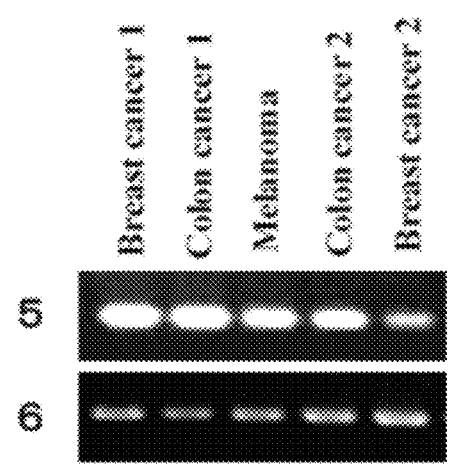
FIG. 3 shows the expression patterns of the identified KATNAL1 gene in mouse normal tissues, tumor tissues and cancer cell lines. Reference numeral 5, the expression patterns of the mouse KATNAL1 gene in various mouse tissues and cell lines; reference numeral 6, the expression patterns of the mouse GAPDH gene in various mouse tissues and cell lines.

Expression of the genes obtained by the above method in dog, human and mouse normal tissues and various cell lines were investigated by the RT-PCR (Reverse Transcription-PCR) method. The reverse transcription reaction was carried out as follows. That is, from 50 to 100 mg of each tissue or 5×10$^6$ to 10×10$^6$ cells of each cell line, total RNA was extracted using the TRIZOL™ reagent (manufactured by Invitrogen) (a monophasic solution of phenol, guanidine isothiocyanate, and other components which facilitate the isolation of a variety of RNA species of large or small molecular size) according to the protocol described in the attached instructions. Using this total RNA, cDNA was synthesized with the SUPERSCRIPT™ First-Strand Synthesis System for RT-PCR (manufactured by Invitrogen) (to synthesize first-strand cDNA from purified poly(A)+ or total RNA using the following: Oligo(dT) 12-18 (0.5 µg/µl), Random hexamers (50 ng/µl), 10× RT buffer (20 mM Tris-HCl, pH 8.4, 500 mM KCl, 25 mM MgCl$_2$), 25 mM Magnesium Chloride, 0.1 M DTT, 10 mM dNTP mix, SUPERSCRIPT™ II RT (Reverse Transcriptase) (50 U/µl), RNASEOUT™ (40 U/µl) (Recombinant Ribonuclease Inhibitor), *E. coli* RNase H (2 U/µl), DEPC-treated water, Control RNA (50 ng/µl), Control Primer A (10 µM), Control Primer B (10 µM)) according to the protocol described in the attached instructions. As the cDNAs of human normal tissues (brain, hippocampus, testis, colon and placenta), Gene Pool cDNA (manufactured by Invitrogen), Clone QUICK-CLONE™ cDNA (manufactured by CLONETECH) (double-stranded cDNA, purified to remove interfering RNA and genomic DNA and Large-Insert cDNA Library (manufactured by CLONETECH) were used. The PCR reaction was carried out using primers specific to the obtained gene (the dog primers shown in SEQ ID NOs:15 and 16, the human primers shown in SEQ ID NOs:17 and 18, and the mouse primers shown in SEQ ID NOs:19 and 20) as described below. That is, the reagents and the attached buffer were mixed such that 0.25 µl of the sample prepared by the reverse transcription reaction, 2 µM each of the above primers, 0.2 mM each of dNTPs, and 0.65 U ExTaq polymerase (manufactured by Takara Shuzo Co., Ltd.) were contained in the resulting mixture in a final volume of 25 µl, and the reaction was carried out by 30 cycles of 94° C. for 30 seconds, 55° C. for 30 seconds and 72° C. for 1 minute using a Thermal Cycler (manufactured by BIO RAD). As a control for comparison, primers specific to GAPDH (the dog and human GAPDH primers are shown in SEQ ID NOs:21 and 22; and the mouse GAPDH primers are shown in SEQ ID NOs:23 and 24) were used at the same time. As a result, as shown in FIG. 1, the dog KATNAL1 gene was not expressed in most of the healthy dog tissues, while the gene was strongly expressed in the dog tumor tissues. Also in terms of the human and mouse KATNAL1 genes, the expression was not observed in most of the normal human and mouse tissues, while the expression was detected in most of the cancer cell lines (FIGS. 2 and 3), as in the case of the dog KATNAL1 gene.

(5) Quantitative Analysis of Expression in Various Tissues

The gene obtained by the above method was subjected to investigation of expression in human normal tissues by the quantitative RT-PCR (Reverse Transcription-PCR) method. As cDNAs for human normal tissues and cancer tissues, Tissue scan Real Time cancer survey Panel I (manufactured by ORIGENE) was used. The quantitative RT-PCR was carried out using CFX96 Real Time Cystem-C1000 Thermal Cycler, manufactured by Bio-Rad Laboratories, Inc. The PCR reaction was carried out as follows using primers specific to the obtained gene (shown in SEQ ID NOs:17 and 18). That is, 5 µl of the cDNA sample, 2 µM each of the primers, and the reagents and the buffer contained in 2× SYBR Premix Ex TaqII polymerase (manufactured by Takara Shuzo Co., Ltd.) were mixed together to prepare a mixture in a final volume of 20 µl, and the reaction was carried out by 30 cycles of 94° C. for 30 seconds, 55° C. for 30 seconds and 72° C. for 1 minute. As a result, the expression level of the KATNAL1 gene in each of breast cancer, colon cancer, thyroid cancer, liver cancer, prostate cancer and lung cancer was not less than 5 times higher than the expression level in its corresponding normal tissue. Based on these results, it can be expected that there is no concern of occurrence of side effects by antitumor agents targeting human KATNAL1 in normal tissues at all, and that the benefit of the pharmacological effect of the agents largely exceeds the risk of their side effects.

Example 2

Analysis of Cancer Antigenicity of KATNAL1 In Vivo (1) Preparation of Recombinant Vector that Expresses KATNAL1 In Vivo Based on the base sequence of SEQ ID NO:5, a recombinant vector that expresses KATNAL1 in vivo was prepared. PCR was prepared from the mouse cancer cell line N2a (purchased from ATCC), which showed the expression in Example 1. The reagents and the attached buffer were mixed such that 1 µl of the cDNA, 0.4 µM each of two kinds of primers having the HindIII and XbaI restriction sites (shown in SEQ ID NOs:25 and 26), 0.2 mM dNTP and 1.25 U PrimeSTAR HS polymerase (manufactured by Takara Shuzo Co., Ltd.) were contained in the resulting mixture in a final volume of 50 µl, and PCR was carried out by 30 cycles of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence of SEQ ID NO:5. After the PCR, the amplified DNA was subjected to electrophoresis using 1% agarose gel, and a DNA fragment of about 1500 bp was purified using QIAQUICK™ Gel Extraction Kit (manufactured by QIAGEN) (a silica membrane assembly for binding of DNA in high-salt buffer and elution with low-salt buffer or water).

The purified DNA fragment was ligated into a cloning vector pCR-Blunt (manufactured by Invitrogen). *E. coli* was transformed with the resulting ligation product, and the plasmid was then recovered. The sequence of the amplified gene fragment was confirmed to be the same as the sequence of interest by sequencing. The plasmid having the sequence of interest was treated with restriction enzymes HindIII and XbaI, and purified using QIAQUICK™ Gel Extraction Kit (a silica membrane assembly for binding of DNA in high-salt buffer and elution with low-salt buffer or water), followed by inserting the gene sequence of interest into a mammalian expression vector pcDNA3.1 (manufactured by Invitrogen) that had been treated with the restriction enzymes HindIII and XbaI. Use of this vector enables production of KATNAL1 protein in mammalian cells.

To 100 µg of the thus prepared plasmid DNA, 50 µg of gold particles (manufactured by Bio Rad), 100 µl of spermidine (manufactured by SIGMA) and 100 µl of 1 M CaCl$_2$ (manufactured by SIGMA) were added, and the resulting mixture was stirred by vortexing, followed by leaving the mixture to stand for 10 minutes at room temperature (the resulting particles are hereinafter referred to as the gold-DNA particles). The mixture was then centrifuged at 3000 rpm for 1 minute and the supernatant was discarded, followed by rinsing the precipitate 3 times with 100% ethanol (manufactured by WAKO). To the gold-DNA particles, 6 ml of 100% ethanol was added, and the resulting mixture was sufficiently stirred by vortexing, followed by pouring the gold-DNA particles into Tefzel Tubing (manufactured by Bio Rad) and allowing the particles to precipitate on the wall surface. Ethanol was removed by air-drying from the Tefzel Tubing to which the gold-DNA particles were attached, and the tube was then cut into pieces having a length that is appropriate for a gene gun.

(2) Antitumor Effect of KATNAL1 by DNA Vaccine Method

The above prepared tube was fixed in a gene gun, and the DNA vaccine was transdermally administered, by application of a pressure of 400 psi using pure helium gas, a total of 3 times at intervals of 7 days to the abdominal cavity of each of 10 individuals of A/J mice (7 weeks old, male, purchased from Japan SLC) and Balb/c mice (7 weeks old, male, purchased from Japan SLC) whose hair had been shaved (this corresponds to inoculation of 2 µg/individual of the plasmid DNA). Thereafter, a mouse neuroblastoma cell line N2a or a colon cancer cell line CT26 was transplanted to each mouse in an amount of 1×10$^6$ cells to evaluate the antitumor effect (prophylactic model). For each model, plasmid DNA containing no KATNAL1 gene inserted was administered to 10 individuals of mice to provide a control.

The antitumor effect was evaluated based on the size of the tumor (major axis×minor axis$^2$/2) and the ratio of living mice. As a result of this study, in the prophylactic model using the neuroblastoma cell line, the size of the tumor became 2886 mm$^3$ and 659 mm$^3$ on Day 43 in the control group and the KATNAL1 plasmid-administered group, respectively. Thus, remarkable regression of the tumor was observed in the KATNAL1 plasmid-administered group. Further, as a result of observation of survival in the prophylactic model using the neuroblastoma cell line, it was found that all cases died by Day 76 after the administration in the control group, while 60% of the mice survived in the KATNAL1 plasmid-administered group. These results indicate a significant antitumor effect in the KATNAL1 plasmid-administered group as compared to the control group. Similarly, in the prophylactic model using the colon cancer cell line, the size of the tumor became 2598 mm$^3$ and 763 mm$^3$ on Day 35 in the control group and the KATNAL1 plasmid-administered group, respectively. Thus, remarkable regression of the tumor was observed in the KATNAL1 plasmid-administered group. Further, as a result of observation of survival, it was found that all cases died by Day 50 after the administration in the control group, while 50% of the mice survived in the KATNAL1 plasmid-administered group. These results indicate a significant antitumor effect in the KATNAL1 plasmid-administered group as compared to the control group.

Example 3

Preparation of Human Recombinant KATNAL1 Protein and Evaluation of its Immunity-Inducing Ability (1) Preparation of Human Recombinant KATNAL1 Protein Based on the base sequence of SEQ ID NO:3, a recombinant protein of human KATNAL1 was prepared. The regents and the attached buffer were mixed such that 1 µl of the cDNA prepared in Example 1 whose expression could be confirmed for cDNAs from various tissues and cells by the RT-PCR method, 0.4 µM each of two kinds of primers having the EcoRI and XhoI restriction sites (shown in SEQ ID NOs:27 and 28), 0.2 mM dNTP and 1.25 U PrimeSTAR HS polymerase (manufactured by Takara Shuzo Co., Ltd.) were contained in the resulting mixture in a final volume of 50 µl, and PCR was carried out by 30 cycles of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence of SEQ ID NO:4. After the PCR, the amplified DNA was subjected to electrophoresis using 1% agarose gel, and a DNA fragment of about 1500 bp was purified using QIAQUICK™ Gel Extraction Kit (manufactured by QIAGEN) (a silica membrane assembly for binding of DNA in high-salt buffer and elution with low-salt buffer or water).

The purified DNA fragment was ligated into a cloning vector pCR-Blunt (manufactured by Invitrogen). *E. coli* was transformed with the resulting ligation product, and the plasmid was then recovered. The sequence of the amplified gene fragment was confirmed to be the same as the sequence of interest by sequencing. The plasmid having the sequence of interest was treated with restriction enzymes EcoRI and XhoI, and purified using QIAQUICK™ Gel Extraction Kit (a silica membrane assembly for binding of DNA in high-salt buffer and elution with low-salt buffer or water), followed by inserting the gene sequence of interest into an expression vector for *E. coli*, pET30a (manufactured by Novagen) that had been treated with the restriction enzymes EcoRI and XhoI. Use of this vector enables production of a His tag-fused recombinant protein. *E. coli* for expression, BL21 (DE3), was transformed with this plasmid, and expression was induced with 1 mM IPTG, to allow expression of the protein of interest in *E. coli*.

(2) Purification of Recombinant KATNAL1 Protein

The thus obtained recombinant *E. coli* that expresses SEQ ID NO:4 was cultured in LB medium supplemented with 100 µg/ml ampicillin at 37° C. until the absorbance at 600 nm reached about 0.7, and isopropyl-β-D-1-thiogalactopyranoside was then added to the culture at a final concentration of 1 mM, followed by further culturing the recombinant *E. coli* at 37° C. for 4 hours. Subsequently, the bacterial cells were collected by centrifugation at 4,800 rpm for 10 minutes. The pellet of the bacterial cells was suspended in phosphate-buffered saline and further subjected to centrifugation at 4,800 rpm for 10 minutes, to wash the bacterial cells.

The bacterial cells were suspended in 50 mM Tris-HCl buffer (pH 8.0) and subjected to sonication on ice. The liquid obtained by the sonication of *E. coli* was centrifuged at 6000 rpm for 20 minutes, to obtain the supernatant as the soluble fraction and the precipitate as the insoluble fraction.

The insoluble fraction was suspended in 50 mM Tris-HCl buffer (pH 8.0) and then centrifuged at 6000 rpm for 15 minutes. This operation was repeated twice for removal of proteases.

The residue was suspended in 50 mM Tris-HCl buffer (pH 8.0) supplemented with 6 M guanidine hydrochloride and 0.15 M sodium chloride, and left to stand at 4° C. for 20 hours to denature protein. Thereafter, the suspension was centrifuged at 6000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 50 mM Tris-HCl buffer (pH 8.0) supplemented with 6M guanidine hydrochloride and 0.15 M sodium chloride), followed by leaving the resultant to stand at 4° C. overnight to allow adsorption to the nickel-chelated carrier. The column carrier was centrifuged at 1500 rpm for 5 minutes and the resulting supernatant was recovered. The column carrier was then suspended in phosphate-buffered saline and refilled into the column.

The fraction not adsorbed to the column was washed with 10 column volumes of 0.1 M acetate buffer (pH 4.0) supplemented with 0.5 M sodium chloride, and immediately thereafter, elution with 0.1 M acetate buffer (pH 3.0) supplemented with 0.5 M sodium chloride was carried out to obtain a purified fraction, which was used later as the material for an administration test. The presence of the protein of interest in each eluted fraction was confirmed by Coomassie staining carried out according to a conventional method.

The buffer of the purified preparation obtained by the above method was replaced with a reaction buffer (50 mM Tris-HCl, 100 mM NaCl, 5 mM $CaCl_2$ (pH8.0)), and the resulting sample was subjected to cleavage of the His tag with factor Xa protease and purification of the protein of interest, using Factor Xa Cleavage Capture Kit (manufactured by Novagen) in accordance with the protocol attached to the kit. Subsequently, the buffer of 12 ml of the purified preparation obtained by the above method was replaced with physiological phosphate buffer (manufactured by Nissui Pharmaceutical) using ultrafiltration NANOSEP 10K OMEGA (manufactured by PALL), and the resulting sample was subjected to aseptic filtration through HT Tuffryn Acrodisc 0.22 µm (manufactured by PALL) and used in the experiment.

(3) Induction of CD8-Positive Cytotoxic T Cells Reactive with Human Recombinant KATNAL1 Protein From a healthy individual, peripheral blood was separated, and the peripheral blood was overlaid on Lymphocyte separation medium (OrganonpTeknika, Durham, N.C.), followed by centrifuging the resultant at 1,500 rpm at room temperature for 20 minutes. A fraction containing peripheral blood mononuclear cells (PBMCs) was recovered and washed 3 (or more) times in cold phosphate buffer, to obtain PBMCs. The obtained PBMCs were suspended in 20 ml of AIM-V medium (Life Technololgies, Inc., Grand Island, N.Y., USA), and the cells were allowed to adhere to a culture flask (Falcon) at 37° C. in 5% $CO_2$ for 2 hours. Nonadherent cells were used for preparation of T cells, and adherent cells were used for preparation of dendritic cells.

On the other hand, the adherent cells were cultured in AIM-V medium in the presence of IL-4 (1000 U/ml) and GM-CSF (1000 U/ml). Nonadherent cells obtained 6 days later were collected, and the human recombinant KATNAL1 protein was added to the cells at a concentration of 10 µg/ml, followed by culturing the cells at 37° C. in 5% $CO_2$ for 4 hours. Thereafter, the medium was replaced with AIM-V medium supplemented with IL-4 (1000 U/ml), GM-CSF (1000 U/ml), IL-6 (1000 U/ml, Genzyme, Cambridge, Mass.), IL-1β (10 ng/ml, Genzyme, Cambridge, Mass.) and TNF-α (10 ng/ml, Genzyme, Cambridge, Mass.), and the culture was carried out for additional 2 days to obtain a population of nonadherent cell to be used as dendritic cells.

The prepared dendritic cells were suspended in AIM-V medium at a cell density of $1 \times 10^6$ cells/ml, and the human recombinant KATNAL1 protein was added again at a concentration of 10 µg/ml to the suspension. Using a 96-well plate, the cells were cultured at 37° C. in 5% $CO_2$ for 4 hours. After the culture, X-ray irradiation (3000 rads) was carried out, and the cells were washed with AIM-V medium, followed by suspension in AIM-V medium supplemented with 10% human AB serum (Nabi, Miami, Fla.), IL-6 (1000 U/ml) and IL-12 (10 ng/ml, Genzyme, Cambridge, Mass.). The cells were then placed in a 24-well plate in an amount of $1 \times 10^5$ cells/well. Further, the prepared T cell population was added to each well in an amount of $1 \times 10^6$ cells, and cultured at 37° C. in 5% $CO_2$. Each culture supernatant was discarded 7 days later, and dendritic cells obtained in the same manner as described above by treatment with the human protein and the subsequent X-ray irradiation were suspended in AIM-V medium supplemented with 10% human AB serum (Nabi, Miami, Fla.), IL-7 (10 U/ml, Genzyme, Cambridge, Mass.) and IL-2 (10 U/ml, Genzyme, Cambridge, Mass.) (cell density, $1 \times 10^5$ cells/ml). The resulting suspension was added to the 24-well plate in an amount of 1×10⁵ cells/well, and the cells were further cultured. After repeating the same operation 4 to 6 times at intervals of 7 days, stimulated T cells were recovered, and induction of CD8-positive T cells was confirmed by flow cytometry.

As a negative control, a protein having a sequence that is outside the scope of the present invention was used (SEQ ID NO:29).

Subsequently, whether or not the CD8-positive T cells stimulated with the present polypeptide can damage the expressing tumor cells was studied.

In a 50-ml centrifuge tube, 10⁵ cells of a malignant brain tumor cell line, T98G (Stein G H et al., J. Cell Physiol., 99:43-54 (1979); purchased from ATCC), in which the expression was confirmed, were collected, and 100 µCi chromium 51 was added to the cells, followed by incubation of the resulting mixture at 37° C. for 2 hours. Thereafter, the cells were washed 3 times with AIM-V medium supplemented with 10% human AB serum, and placed in a 96-well V-bottom plate in an amount of 10³ cells per well. Subsequently, 10⁵, 5×10⁴, 2.5×10⁴ or 1.25×10⁴ CD8-positive T cells that were stimulated with the human recombinant protein and suspended in AIM-V medium supplemented with 10% human AB serum were added to each well, and culture was performed at 37° C. in 5% CO₂ for 4 hours. Thereafter, the amount of chromium 51 released from damaged tumor cells in the culture supernatant was measured using a gamma counter to calculate the cytotoxic activity of the CD8-positive T cells stimulated with the human recombinant protein.

As a result, it was found that the CD8-positive T cells stimulated with the human recombinant protein had cytotoxic activity against T98G. On the other hand, the CD8-positive T cells induced using the negative control protein (SEQ ID NO:29) did not show cytotoxic activity. Thus, it was revealed that the human recombinant protein used in the present invention has a capacity to induce CD8-positive cytotoxic T cells that can damage tumor cells.

The cytotoxic activity means the cytotoxic activity of the CD8-positive T cells against T98G determined by: mixing 10⁵ CD8-positive T cells stimulated and induced as described above, with 10³ cells of the malignant brain tumor cell line T98G into which chromium 51 was incorporated; culturing the resulting mixture for 4 hours; measuring the amount of chromium 51 released to the medium after the culture; and then performing calculation according to Equation 1.

Cytotoxic activity (%)=amount of chromium 51 released from T98G after addition of CD8-positive T cells (cpm)/amount of chromium 51 released from target cells after addition of 1 N hydrochloric acid (cpm)×100.         Equation 1

INDUSTRIAL APPLICABILITY

The present invention is useful for therapy and/or prophylaxis of cancer since the present invention provides an immunity-inducing agent containing a polypeptide that exerts antitumor activity against various cancers.

---

The invention claimed is:

1. A method for inducing cytotoxic T cell(s) for therapy of a cancer(s), said method comprising:
administering to an individual with cancer an effective amount to induce cytotoxic T cell(s) of at least one polypeptide selected from the polypeptides (a) below, and/or a recombinant vector(s) that comprise(s) a polynucleotide(s) encoding said at least one polypeptide, said recombinant vector(s) being capable of expressing said polypeptide(s) in vivo:
(a) a polypeptide of the amino acid sequence of SEQ ID NOs: 2, 4, 8, 10 or 12,
wherein said cancer(s) is/are a cancer(s) expressing KATNAL1,
wherein the cancer is neuroblastoma or colon cancer.

2. The method according to claim 1, further comprising administering an immunoenhancer.

3. The method according to claim 2, wherein said immunoenhancer is at least one selected from the group consisting of Freund's incomplete adjuvant, Montanide, poly-I:C, CpG oligonucleotides, interleukin-12, interleukin-18, interferon-α, interferon-β, interferon-ω, interferon-γ, and Flt3 ligand.

4. The method according to claim 1, said method comprising:
administering to an individual with cancer at least any one of (i) to (iii) below:
(i) the polypeptide or vector;
(ii) a cytotoxic T cell that selectively binds a complex comprising at least one said polypeptide incorporated into an MHC molecule; and/or
(iii) an antigen-presenting cell which presents on its surface a complex comprising at least one said polypeptide incorporated into a MHC molecule.

5. The method of claim 1, wherein the polypeptide is administered as a polypeptide.

6. A method for inducing immunity for therapy of a cancer(s), said method comprising:
administering to an individual with cancer at least one polypeptide selected from the polypeptides (a) below, and/or a recombinant vector(s) that comprise(s) a polynucleotide(s) encoding said at least one polypeptide, said recombinant vector(s) being capable of expressing said polypeptide(s) in vivo:
(a) a polypeptide of the amino acid sequence of SEQ ID NOs: 2, 4, 8, 10 or 12,
wherein said cancer(s) is/are a cancer(s) expressing KATNAL1, and
wherein the cancer is neuroblastoma or colon cancer.

* * * * *